US011202448B2

(12) United States Patent
MacLean et al.

(10) Patent No.: US 11,202,448 B2
(45) Date of Patent: Dec. 21, 2021

(54) VOLATILE APPLICATIONS AGAINST PATHOGENS

(71) Applicant: AGROFRESH INC., Philadelphia, PA (US)

(72) Inventors: Daniel MacLean, Woodland, CA (US); David H. Young, Carmel, IN (US); Richard M. Jacobson, Chalfont, PA (US); Maurice C. Yap, Zionsville, IN (US); Rodrigo A. Cifuentes, Santiago (CL); Donald H. Devries, Fishers, IN (US); Joseph D. Eckelbarger, Carmel, IN (US)

(73) Assignee: AGROFRESH INC., Philadelphia, PA (US)

( * ) Notice: Subject to any disclaimer, the term of this patent is extended or adjusted under 35 U.S.C. 154(b) by 0 days.

(21) Appl. No.: 16/898,916

(22) Filed: Jun. 11, 2020

(65) Prior Publication Data

US 2020/0296967 A1 Sep. 24, 2020

Related U.S. Application Data

(60) Continuation of application No. 16/123,735, filed on Sep. 6, 2018, now Pat. No. 10,765,117, which is a continuation of application No. 15/445,247, filed on Feb. 28, 2017, now Pat. No. 10,070,649, which is a continuation-in-part of application No. 14/690,929, filed on Apr. 20, 2015, now Pat. No. 9,585,396, and a continuation-in-part of application No. 14/294,057, filed on Jun. 2, 2014, now Pat. No. 9,426,996, which is a continuation of application No. 14/167,093, filed on Jan. 29, 2014, now Pat. No. 9,138,001, said application No. 14/690,929 is a continuation-in-part of application No. 14/182,793, filed on Feb. 18, 2014, now Pat. No. 9,138,002, which is a division of application No. 13/945,577, filed on Jul. 18, 2013, now Pat. No. 8,669,207.

(60) Provisional application No. 61/991,821, filed on May 12, 2014, provisional application No. 61/758,313, filed on Jan. 30, 2013, provisional application No. 61/831,187, filed on Jun. 5, 2013.

(51) Int. Cl.
| | |
|---|---|
| *A01N 55/08* | (2006.01) |
| *A01N 25/18* | (2006.01) |
| *A23L 3/3445* | (2006.01) |
| *A01N 55/00* | (2006.01) |
| *A23B 4/16* | (2006.01) |
| *A23B 4/20* | (2006.01) |
| *A23B 7/152* | (2006.01) |
| *A23B 7/154* | (2006.01) |
| *A61K 9/00* | (2006.01) |
| *A61K 9/70* | (2006.01) |
| *A61K 31/69* | (2006.01) |

(52) U.S. Cl.
CPC ............. *A01N 55/08* (2013.01); *A01N 25/18* (2013.01); *A01N 55/00* (2013.01); *A23B 4/16* (2013.01); *A23B 4/20* (2013.01); *A23B 7/152* (2013.01); *A23B 7/154* (2013.01); *A23L 3/3445* (2013.01); *A61K 9/0034* (2013.01); *A61K 9/70* (2013.01); *A61K 31/69* (2013.01)

(58) Field of Classification Search
CPC .................................................... A01N 55/08
USPC ....................................................... 549/213
See application file for complete search history.

(56) References Cited

U.S. PATENT DOCUMENTS

| | | | |
|---|---|---|---|
| 3,686,398 A | 8/1972 | Kohn | |
| 3,873,279 A | 3/1975 | Michael | |
| 4,421,774 A | 12/1983 | Vidal | |
| 4,843,956 A | 7/1989 | Lashlee | |
| 5,880,188 A | 3/1999 | William | |
| 5,958,463 A | 9/1999 | Milne | |
| 6,305,148 B1 | 10/2001 | Bowden | |
| 7,078,546 B2 | 7/2006 | Edward | |
| 7,119,049 B2 | 10/2006 | Heiko | |
| 7,176,228 B2 | 2/2007 | Hans-Ludwig | |
| 7,179,840 B2 | 2/2007 | Heiko | |
| 7,208,169 B2 | 4/2007 | Ralf | |
| 7,390,806 B2 | 6/2008 | Lee | |
| 7,393,856 B2 | 7/2008 | Bellinger-Kawahara | |
| 7,465,836 B2 | 12/2008 | Lee | |
| 7,582,621 B2 | 9/2009 | Baker | |
| 7,652,000 B2 | 1/2010 | David | |
| 7,767,657 B2 | 8/2010 | Baker | |
| 7,816,344 B2 | 10/2010 | Baker | |
| 7,842,823 B2 | 11/2010 | Chang | |
| 7,888,356 B2 | 2/2011 | Lee | |
| 7,968,752 B2 | 6/2011 | Lee | |

(Continued)

FOREIGN PATENT DOCUMENTS

| | | |
|---|---|---|
| AU | 2010203096 | 8/2010 |
| AU | 2012327171 | 6/2013 |

(Continued)

OTHER PUBLICATIONS

Dauthy, "Fruit and Vegetable processing: Chapter 5.3 Chemical Preservation," FAO Argricultural Services Bulletin, 1995, 119.

(Continued)

*Primary Examiner* — Taofiq A Solola
(74) *Attorney, Agent, or Firm* — Barnes & Thornburg LLP

(57) ABSTRACT

This invention is related to the use of a volatile antimicrobial compound against pathogens. The volatile antimicrobial compounds provided include certain oxaborole compounds, for example benzoxaboroles. Delivery systems are provided to take advantage of the volatile nature of these antimicrobial compounds. The method and use disclosed can be combined with other volatile compounds.

20 Claims, No Drawings

(56) References Cited

U.S. PATENT DOCUMENTS

| | | |
|---|---|---|
| 8,039,450 B2 | 10/2011 | Tsutomu |
| 8,039,451 B2 | 10/2011 | Baker |
| 8,106,031 B2 | 1/2012 | Lee |
| 8,110,259 B2 | 2/2012 | Siegel |
| 8,115,026 B2 | 2/2012 | Baker |
| 8,168,614 B2 | 5/2012 | Baker |
| 8,343,944 B2 | 1/2013 | Xia |
| 8,436,028 B2 | 5/2013 | Hunt |
| 8,440,642 B2 | 5/2013 | Baker |
| 8,461,134 B2 | 6/2013 | Hernandez |
| 8,461,135 B2 | 6/2013 | Tsutomu |
| 8,461,336 B2 | 6/2013 | Yasheen |
| 8,461,364 B2 | 6/2013 | Conrad |
| 8,470,803 B2 | 6/2013 | Tsutomu |
| 8,501,712 B2 | 8/2013 | Baker |
| 8,546,357 B2 | 10/2013 | Tsutomu |
| 8,669,207 B1 | 3/2014 | Martin |
| 8,791,258 B2 | 7/2014 | Chang |
| 8,906,848 B2 | 12/2014 | Wuts |
| 9,138,001 B2 | 9/2015 | Daniel |
| 9,138,002 B2 | 9/2015 | Martin |
| 9,145,429 B2 | 9/2015 | Kurt |
| 9,185,914 B2 | 11/2015 | Jens |
| 9,309,508 B2 | 4/2016 | Stephen |
| 9,346,834 B2 | 5/2016 | Huchen |
| 9,426,996 B2 | 8/2016 | Daniel |
| 9,493,489 B2 | 11/2016 | Robert |
| 9,493,490 B1 | 11/2016 | Tsutomu |
| 9,512,148 B2 | 12/2016 | Chellappan |
| 9,572,823 B2 | 2/2017 | Baker |
| 9,585,396 B2 | 3/2017 | Tim |
| 9,617,285 B2 | 4/2017 | Tsutomu |
| 9,676,796 B2 | 6/2017 | Soon-Hoe |
| 9,730,454 B2 | 8/2017 | Jacobson |
| 9,737,075 B2 | 8/2017 | Stephen |
| 9,889,146 B2 | 2/2018 | Alley |
| 9,944,660 B2 | 4/2018 | Ajay |
| 10,011,616 B2 | 7/2018 | Yong-Kang |
| 10,040,806 B2 | 8/2018 | Ramya |
| 10,051,864 B2 | 8/2018 | Andre |
| 10,070,649 B2 | 9/2018 | Tim |
| 10,159,252 B2 | 12/2018 | Jacobson |
| 10,765,117 B2 | 9/2020 | Maclean |
| 2004/0259842 A1 | 12/2004 | Katsuhiko |
| 2007/0155699 A1 | 7/2007 | Baker |
| 2007/0286822 A1 | 12/2007 | Virginia |
| 2007/0293457 A1 | 12/2007 | Baker |
| 2008/0153992 A1 | 6/2008 | Wilfred |
| 2008/0293675 A1 | 11/2008 | Lee |
| 2008/0317737 A1 | 12/2008 | Bhiku |
| 2009/0148623 A1 | 6/2009 | Sandmeier |
| 2009/0170861 A1 | 7/2009 | Ting |
| 2009/0227541 A1 | 9/2009 | Baker |
| 2009/0239824 A1 | 9/2009 | Lee |
| 2009/0291917 A1 | 11/2009 | Tsutomu |
| 2010/0004205 A1 | 1/2010 | Mayer |
| 2010/0158992 A1 | 6/2010 | Black |
| 2010/0190748 A1 | 7/2010 | Baker |
| 2010/0256092 A1 | 10/2010 | Xia |
| 2010/0267981 A1 | 10/2010 | Baker |
| 2010/0292504 A1 | 11/2010 | Baker |
| 2011/0059985 A1 | 3/2011 | Schmidts |
| 2011/0076261 A1 | 3/2011 | Bhiku |
| 2011/0082118 A1 | 4/2011 | Bhiku |
| 2011/0123624 A1 | 5/2011 | Michael |
| 2011/0124597 A1 | 5/2011 | Hernandez |
| 2011/0136763 A1 | 6/2011 | Xia |
| 2011/0152217 A1 | 6/2011 | Conrad |
| 2011/0166103 A1 | 7/2011 | Tsutomu |
| 2011/0166104 A1 | 7/2011 | Yasheen |
| 2011/0172187 A1 | 7/2011 | Hernandez |
| 2011/0183969 A1 | 7/2011 | Michael |
| 2011/0190235 A1 | 8/2011 | Daitao |
| 2011/0207701 A1 | 8/2011 | Huchen |
| 2011/0207702 A1 | 8/2011 | Robert |
| 2011/0212918 A1 | 9/2011 | Hernandez |
| 2011/0319361 A1 | 12/2011 | Baker |
| 2012/0035132 A1 | 2/2012 | Kurt |
| 2012/0115813 A1 | 5/2012 | Hernandez |
| 2012/0214765 A1 | 8/2012 | Tsutomu |
| 2012/0264714 A1 | 10/2012 | Baker |
| 2012/0289686 A1 | 11/2012 | Baker |
| 2012/0295875 A1 | 11/2012 | Huchen |
| 2013/0059802 A1 | 3/2013 | Baker |
| 2013/0059803 A1 | 3/2013 | Baker |
| 2013/0064783 A1 | 3/2013 | Baker |
| 2013/0131016 A1 | 5/2013 | Tsutomu |
| 2013/0131017 A1 | 5/2013 | Tsutomu |
| 2013/0165411 A1 | 6/2013 | Gordeev |
| 2013/0196433 A1 | 8/2013 | Raines |
| 2013/0210770 A1 | 8/2013 | Baker |
| 2013/0231304 A1 | 9/2013 | Jacobs |
| 2013/0244980 A1 | 9/2013 | Baker |
| 2013/0298290 A1 | 11/2013 | Johannes |
| 2013/0316979 A1 | 11/2013 | Baker |
| 2014/0088041 A1 | 3/2014 | Bernd |
| 2014/0155305 A1 | 6/2014 | Seth |
| 2014/0259230 A1 | 9/2014 | Carla |
| 2015/0202321 A1 | 7/2015 | Abu |
| 2016/0199351 A1 | 7/2016 | Rappleye |
| 2016/0340369 A1 | 11/2016 | Daitao |
| 2017/0000132 A1 | 1/2017 | Ramya |
| 2017/0000133 A1 | 1/2017 | Ramya |
| 2017/0037258 A1 | 2/2017 | Benkovic |
| 2017/0042966 A1 | 2/2017 | Van Der Weerden |
| 2017/0216327 A1 | 8/2017 | Dina |
| 2017/0251673 A1 | 9/2017 | Rodrigo |
| 2017/0280724 A1 | 10/2017 | Jacobson |
| 2017/0295809 A1 | 10/2017 | Timothy |
| 2017/0319536 A1 | 11/2017 | Roman |
| 2017/0327519 A1 | 11/2017 | Tsutomu |
| 2017/0340607 A1 | 11/2017 | Sibley |
| 2017/0355719 A1 | 12/2017 | Hernandez |
| 2018/0000089 A1 | 1/2018 | Daniel |
| 2018/0000090 A1 | 1/2018 | Ramya |
| 2018/0009831 A1 | 1/2018 | Ravishanker |
| 2018/0016285 A1 | 1/2018 | Baker |
| 2018/0065994 A1 | 3/2018 | Tsutomu |
| 2018/0139975 A1 | 5/2018 | Timothy |
| 2018/0179229 A1 | 6/2018 | Antonio |
| 2018/0179233 A1 | 6/2018 | Soya |
| 2018/0201628 A1 | 7/2018 | James |
| 2018/0213781 A1 | 8/2018 | Michel |
| 2018/0220654 A1 | 8/2018 | Jacobson |
| 2018/0230169 A1 | 8/2018 | Ramanujachary |
| 2018/0244699 A1 | 8/2018 | Ramya |

FOREIGN PATENT DOCUMENTS

| | | |
|---|---|---|
| AU | 2012327230 | 7/2013 |
| CA | 2190155 | 12/1995 |
| CA | 2635680 | 7/2007 |
| CA | 2642583 | 8/2007 |
| CA | 2680587 | 9/2008 |
| CN | 101505603 | 8/2009 |
| DE | 102012006458 A1 | 9/2013 |
| EP | 3765331 | 4/1997 |
| EP | 1444981 | 8/2004 |
| EP | 1765358 | 3/2007 |
| EP | 1765360 | 3/2007 |
| EP | 1980564 | 10/2008 |
| EP | 2343304 | 7/2011 |
| EP | 2564857 | 3/2013 |
| GB | 961280 | 6/1964 |
| GB | 1006336 | 9/1965 |
| GB | 1396904 | 6/1975 |
| WO | 1995031970 | 11/1995 |
| WO | 199533754 | 12/1995 |
| WO | 1998021945 | 5/1998 |
| WO | 2005087742 | 9/2005 |
| WO | 2006089067 | 8/2006 |
| WO | 2006102604 | 9/2006 |
| WO | 2007071632 | 6/2007 |
| WO | 2007078340 | 7/2007 |

(56) References Cited

FOREIGN PATENT DOCUMENTS

| | | |
|---|---|---|
| WO | 2007079119 | 7/2007 |
| WO | 2007095638 | 8/2007 |
| WO | 2007131072 | 11/2007 |
| WO | 2007146965 | 12/2007 |
| WO | 2008064345 | 5/2008 |
| WO | 2008070257 | 6/2008 |
| WO | 2008115385 | 9/2008 |
| WO | 2008156798 | 12/2008 |
| WO | 2008157726 | 12/2008 |
| WO | 2009046098 | 4/2009 |
| WO | 2009053741 | 4/2009 |
| WO | 2009111676 | 9/2009 |
| WO | 2009130481 | 10/2009 |
| WO | 2009140309 | 11/2009 |
| WO | 2009144473 | 12/2009 |
| WO | 2010027975 | 3/2010 |
| WO | 2010028005 | 3/2010 |
| WO | 2010045503 | 4/2010 |
| WO | 2010045505 | 4/2010 |
| WO | 2010080558 | 7/2010 |
| WO | 2010136475 | 12/2010 |
| WO | 2011017125 | 2/2011 |
| WO | 2011019612 | 2/2011 |
| WO | 2011019616 | 2/2011 |
| WO | 2011019618 | 2/2011 |
| WO | 2011022337 | 2/2011 |
| WO | 2011037731 | 3/2011 |
| WO | 2011043817 | 4/2011 |
| WO | 2011049971 | 4/2011 |
| WO | 2011060196 | 5/2011 |
| WO | 2011060199 | 5/2011 |
| WO | 2011063293 | 5/2011 |
| WO | 2011094450 | 8/2011 |
| WO | 2011116348 | 9/2011 |
| WO | 2011150190 | 12/2011 |
| WO | 2012033858 | 3/2012 |
| WO | 2012067663 | 5/2012 |
| WO | 2012069652 | 5/2012 |
| WO | 2012139134 | 10/2012 |
| WO | 2012154213 | 11/2012 |
| WO | 2013033270 | 3/2013 |
| WO | 2013050591 | 4/2013 |
| WO | 2013057740 | 4/2013 |
| WO | 2013058824 | 4/2013 |
| WO | 2013078070 | 5/2013 |
| WO | 2013078071 | 5/2013 |
| WO | 2013093615 | 6/2013 |
| WO | 2013108024 | 7/2013 |
| WO | 2013110005 | 7/2013 |
| WO | 2013154759 | 10/2013 |
| WO | 2015097237 | 2/2015 |
| WO | 2016015094 | 2/2016 |
| WO | 2016151293 | 9/2016 |
| WO | 2017102565 | 6/2017 |
| WO | 2017125835 | 7/2017 |
| WO | 2017136930 | 8/2017 |
| WO | 2017180695 | 10/2017 |
| WO | 2017183043 | 10/2017 |
| WO | 2017207358 A1 | 12/2017 |
| WO | 2017216191 A1 | 12/2017 |
| WO | 2017216722 A2 | 12/2017 |
| WO | 2018060140 A1 | 4/2018 |
| WO | 2018102261 | 6/2018 |
| WO | 2018156554 A1 | 8/2018 |
| WO | 2018160845 A1 | 9/2018 |

OTHER PUBLICATIONS

Brown et al., "Convenient Procedures for the Preparation of Alkyl Borate Esters," Proc. for Prepn. Alkyl Borate Esters, Aug. 5, 1956, pp. 3613-3614.
Kumar, J.S. et al., "Development of Practical Methodologies for the Synthesis of Functionalized Benzoboroxoles", Tetrahendron Letters, Elsevier, Amsterdam, NL, col. 51, No. 34, Aug. 24, 2010, pp. 4482-4485.
Mao, W., "AN2690, a topical antifungal agent in development for the treatment of onychmycosis represents a new class and has a novel mechanism of action", Anacor Pharmaceuticals AG, Aug. 20, 2008, XP007921849, www.anacor.com/pdf/SID_p769.pdf [retrieved on Jul. 11, 2013]. XP007921849, wwww.
Ding et al., "Design, Synthesis, and Structure—Activity Relationship of Trypanosoma brucei Leucyl-tRNA Synthetase Inhibitors as Antitrypanosomal Agents," J. Med. Chem. (2011), vol. 54(5), pp. 1276-1287.
Alexander, C. et al., "Imprinted Polymers as Protecting Groups for Regioselective Modifcation of Polyfunctional Substrates," J. Am. Chem. Soc., 1999, 121, 6640-6651.
Haynes et al., "Arylboronic Acids. ViIII. Reactions of Boronophthalide", Noyes Chemical Laboratory, University of Illinois, Nov. 1964, pp. 3229-3233 Urbana, USA (5 pages).
Brown et al. Proc. for Prepn. Alkyl Borate Esters, (1956), pp. 3613-3614.
Shen et al., "Changes of respiration and ethylene production and effects of 1-MCP during the fermentation softening of chinese winter jujube fruit," Zhongguo Nongye Daxue Xuebao (2004) vol. 9(2), pp. 36-39.
Guillen et al., "Efficacy of 1-MCP treatment in tomato fruit 2. Effect of cultivar and ripening stage at harvest," Postharvest Biology and Technol. (2006) vol. 42(3), pp. 235-242.
Carillo et al., "1-Methylcyclopropene delays arazá ripening and improves postharvest fruit quality," LWT-Food Sci. and Tech. (2011) vol. 44, pp. 250-255.
Baker, Stephen et al., Discovery of new boron-containing antifungal agent, 5-fluoro-1,3,dihydroxy-2-1-benzoxabrole (AN2690), for the potential treatment of onychomycosis, Journal of Medicinal Chemistry, Jul. 1, 2006, 49, 4447-4450.
Rock, F.L.W. Matoe, et al., "An Antifungal Agent Inhibits an Aminoacyl-tRNA Synthetase by Trapping tRNA in the Editing Site," Science 316, 2007, 1759-1761.
Reddy et al., "1-MCP, a novel plant growth regulator for regulation of ripening," Agricultural & Horticultural Sciences, 2014.
Pubchem entry for AN2718 (https://pubchem.ncbi.nlm.nih.gov/compound/11845944) accessed Mar. 1, 2020.
Seiradake E, et al., "Antifungal activity and mechanism of action of a benzoxaborole, AN2718, which is in development for the treatment of Tinea pedis," Abstract F1-1176, IDSA Poster Session: New Anti-Fungal Agents (2008).
Mao W, et al., "AN2718 has broad spectrum antifungal activity necessary for the topical treatment of skin and nail fungal infections," Abstract P2422, J. American Acad. Dermatology 60(3) Supplement 1, AB116 (2009).
Rolshausen PE, et al., "Use of boron for the collrol of Eutypa dieback of grapevines," Plant Diseases 89(7): 734-738 (2005).
Qin G, et al., "Inhibitory effect of boron against Botrytis cinerea on table grapes and its possible mechanisms of action," International Journal of Food Microbiology 138: 145-150 (2010).
Thomidis T and Exadaktylou E., "Effect of boron on the development of brown rot (Monilinia laxa) on peaches," Crop Prot. 29: 572-576 (2010).
Expert Declaration of Phillip M. Brannen, Ph.D., filed in an Inter Partes Review of U.S. Pat. No. 10,130,096, filed Nov. 5, 2019.
Boric Acid, Chemical Watch Factsheet, 21, 18-19 (2001).
Ligon JM, et al, "Natural products with antifungal activity from Pseudomonas biocontrol bacteria," Pest Management Science 56: 688-695 (2000).
Alumni Product Registration (Jun. 9, 2010).
Propi-Shield Product Registration (Aug. 11, 2005).
Tilt Label (2006).
Mahmoud YAG, et al., "Recent approaches for collrolling brown spot disease of faba bean in Egypt," Egypt Acad. J. Biol. Sci. 3:41-53 (2011).
Ware G, "Substituted aromatics," pp. 148-149, In: Fundamentals of Pesticides: a self-instruction guide, Tomson Publications, Fresno, CA (1991).

(56) References Cited

OTHER PUBLICATIONS

Bertelsen JR, et al., "Fungicidal effects of azoxystrobin and epoxiconazole on phyllosphere fungi, senescence and yield of winter wheat," Plant Pathology 50:190-205 (2001).
Propi-Shield Label Amendment (Nov. 29, 2006).
Azotech Label Amendment (Sep. 7, 2007).
OptiSHIELD Label (2009).
Abound label (2007).
Chlorosel label (2010).
Ultrex label (2005).
Chloroneb Fact Sheet (2005).
Dichloran Label Amendment (Aug. 5, 2010).
Expert Declaration of Dennis Hall, Ph.D. filed in an Inter Partes Review of U.S. Pat. No. 10,130,096, filed Nov. 5, 2019.
Patent Owner Preliminary Response filed in an Inter Partes Review of U.S. Pat. No. 10,130,096, filed Feb. 18, 2020.
Dictionary Reference filed in an Inter Partes Review of U.S. Pat. No. 10,130,096.
Petition for Inter Partes Review of U.S. Pat. No. 10,130,096, filed Nov. 5, 2019.
Marsh et al., J. Good Sc. 2007, vol. 72, R39-R54.
Edwards, "Organoboron reagents and recent strategies in rhodium catalysed additions," Ph. D. Thesis submitted to University of Bath, 2011, pp. 1-293.
Ma, X. et al., "Synthesis of Boroxine-Linked Aluminium Complexes," Inorg. Chem., 2011, 50, 2010-2014.
Greig, L. et al., "The dynamic covalent chemistry of mono- and bifunctional boroxoaromatics". Tetrahedron, 2006, 63, 2391-2403.
Weike, Z. et al., "Preparation of 2-oxygen derivatives of 1,2-oxaborolane from 2-allyloxy-1,2-oxaborolane," Journal of Organometallic Chemistry, 1990, 387, 131-146.
Office Action for Japanese Patent Application No. 2016-517975, dated Dec. 24, 2019, 4 pages.
International Search Report for PCT/US2014/013510, Dow AgroSciences LLC, Jun. 25, 2014.

VOLATILE APPLICATIONS AGAINST PATHOGENS

CROSS-REFERENCE

This application is a continuation of U.S. patent application Ser. No. 16/123,735, filed Sep. 6, 2018, which is a continuation of U.S. patent application Ser. No. 15/445,247, now U.S. Pat. No. 10,070,649, filed Feb. 28, 2017, which is a continuation-in-part of U.S. patent application Ser. No. 14/690,929, filed on Apr. 20, 2015, which claims the benefit of priority under 35 U.S.C. § 119(e) of U.S. Provisional Patent Application No. 61/991,821, filed May 12, 2014, the content of which is incorporated by reference in its entirety.

U.S. patent application Ser. No. 14/690,929, filed on Apr. 20, 2015, is also a continuation-in-part of U.S. patent application Ser. No. 14/294,057, now U.S. Pat. No. 9,426,996, filed on Jun. 2, 2014, which is a continuation of U.S. patent application Ser. No. 14/167,093, now U.S. Pat. No. 9,138,001, filed on Jan. 29, 2014, which claims the benefit of priority under 35 U.S.C. § 119(e) of U.S. Provisional Patent Application No. 61/758,313, filed Jan. 30, 2013, the contents of all of which are hereby incorporated by reference in their entireties.

U.S. patent application Ser. No. 14/690,929, filed on Apr. 20, 2015, is also a continuation-in-part of U.S. patent application Ser. No. 14/182,793, now U.S. Pat. No. 9,138,002, filed on Feb. 18, 2014, which is a divisional of U.S. patent application Ser. No. 13/945,577, now U.S. Pat. No. 8,669,207, filed on Jul. 18, 2013, which claims the benefit of priority under 35 U.S.C. § 119(e) of 61/831,187, filed Jun. 5, 2013, and U.S. Provisional Patent Application No. 61/758,313, filed Jan. 30, 2013, the contents of all of which are hereby incorporated by reference in their entireties.

BACKGROUND OF THE INVENTION

A number of compounds containing an oxaborole ring have been disclosed previously. However, there has been no teaching that these oxaborole compounds are volatile antimicrobial agents. In addition, these oxaborole compounds have not been used in agricultural applications.

Thus, there remains a need to develop new uses of various volatile antimicrobial agents and/or combinations with a volatile plant growth regulator, in particular for agricultural applications.

SUMMARY OF THE INVENTION

This invention is related to the use of a volatile antimicrobial compound against pathogens affecting meats, plants, or plant parts. The volatile antimicrobial compounds provided include certain oxaborole compounds, for example benzoxaboroles. Delivery systems are provided to take advantage of the volatile nature of these antimicrobial compounds. Also combinations with a volatile plant growth regulator, for example 1-methylcyclopropene (1-MCP), are disclosed.

In one aspect, provided is a method of using a volatile antimicrobial compound against pathogens affecting meats, plants, or plant parts. The method comprises contacting the meats, plants, or plant parts with an effective amount of the volatile antimicrobial compound having a structure of formula (I), (II), or (III):

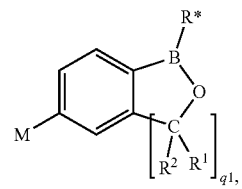
(I)

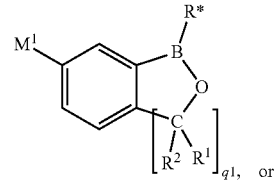
(II)

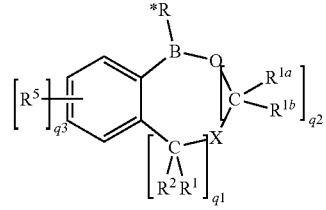
(III)

wherein q1 and q2 are independently 1, 2, or 3;

q3=0, 1, 2, 3, or 4;

M is hydrogen, halogen, —OCH$_3$, or —CH$_2$—O—CH$_2$—O—CH$_3$;

M$^1$ is halogen, —CH$_2$OH, or —OCH$_3$;

X is O, S, or NR$^{1c}$, wherein R$^{1c}$ is hydrogen, substituted alkyl, or unsubstituted alkyl;

R$^1$, R$^{1a}$, R$^{1b}$, R$^2$, and R$^5$ are independently hydrogen, OH, NH$_2$, SH, CN, NO$_2$, SO$_2$, OSO$_2$OH, OSO$_2$NH$_2$, substituted or unsubstituted cycloalkyl, substituted or unsubstituted heterocycloalkyl, substituted or unsubstituted aryl, or substituted or unsubstituted heteroaryl;

R* is substituted or unsubstituted aryl, substituted or unsubstituted arylalkyl, substituted or unsubstituted heteroaryl, substituted or unsubstituted heteroarylalkyl, or substituted or unsubstituted vinyl;

with a proviso that when M is F, R* is not a member selected from:

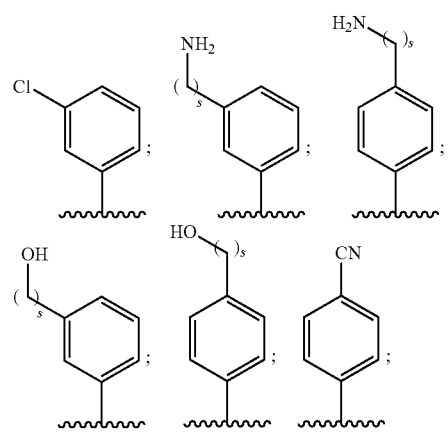

-continued

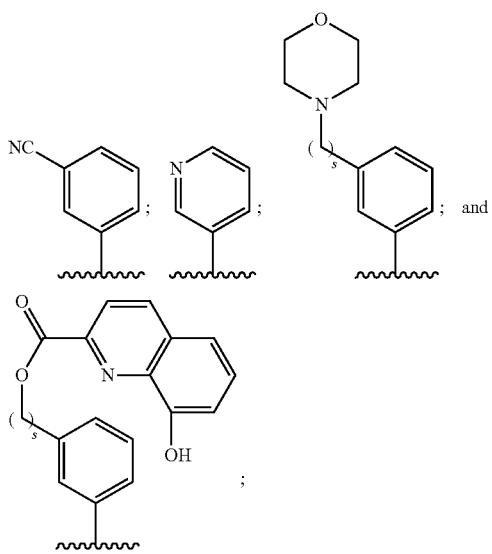

and with a proviso that when M is Cl, R* is not a member selected from:

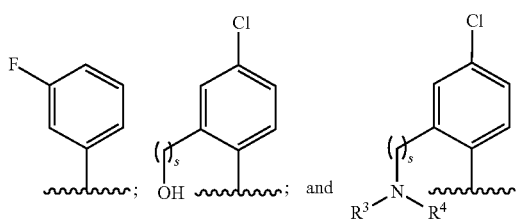

and with a proviso that when M is hydrogen, R* is not a member selected from:

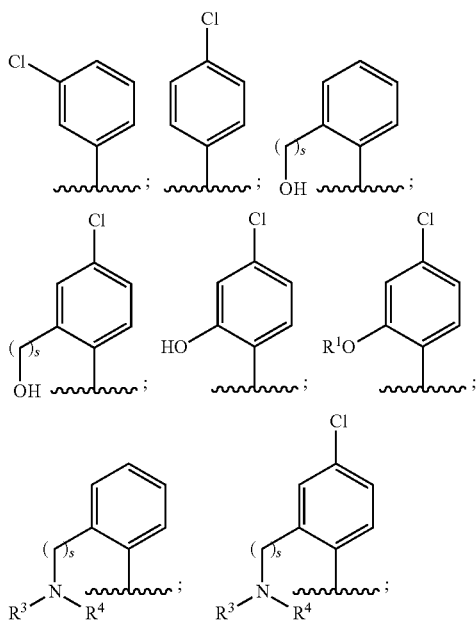

-continued

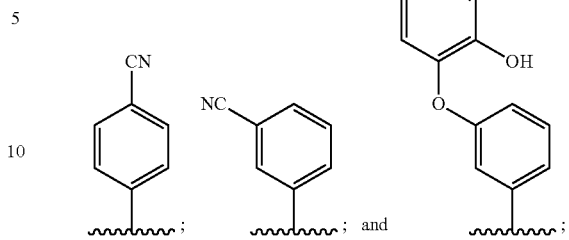

wherein s=1 or 2; and $R^3$ and $R^4$ are independently methyl or ethyl;

and with a provision that when M is $OCH_3$, R* is not a member selected from:

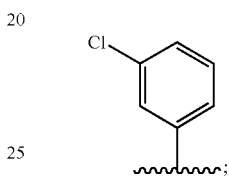

and with a provision that when $M^1$ is F, R* is not a member selected from:

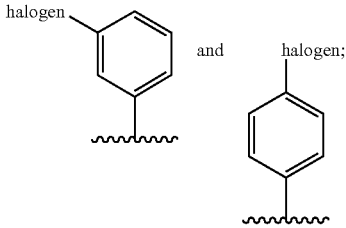

and agriculturally acceptable salts thereof.

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp., *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In another aspect, provided is a method of using a volatile antimicrobial compound against pathogens affecting meats, plants, or plant parts. The method comprises contacting the meats, plants, or plant parts with an effective amount of the volatile antimicrobial compound of formula (IV):

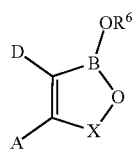

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, ($C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

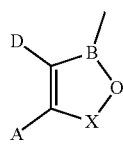

(V)

wherein A, D and X are as defined herein except for boronophthalide;

and agriculturally acceptable salts thereof.

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp.; *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp., *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In one aspect, provided is a method of using a volatile antimicrobial compound against pathogens including human pathogens. The method comprises contacting areas infected by the pathogens with an atmosphere containing an effective amount of the volatile antimicrobial compound in gaseous form, the volatile antimicrobial compound having a structure of formula (I), (II), or (III):

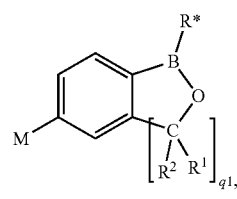

(I)

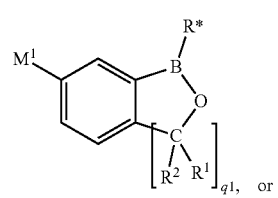

(II)

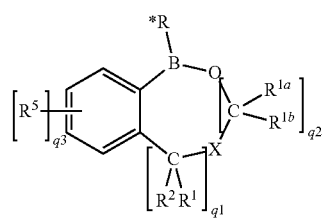

(III)

wherein q1 and q2 are independently 1, 2, or 3;
q3=0, 1, 2, 3, or 4;

M is hydrogen, halogen, —OCH₃, or —CH₂—O—CH₂—O—CH₃;

M¹ is halogen, —CH₂OH, or —OCH₃;

X is O, S, or NR$^{1c}$, wherein R$^{1c}$ is hydrogen, substituted alkyl, or unsubstituted alkyl;

R¹, R$^{1a}$, R$^{1b}$, R², and R⁵ are independently hydrogen, OH, NH₂, SH, CN, NO₂, SO₂, OSO₂OH, OSO₂NH₂, substituted or unsubstituted cycloalkyl, substituted or unsubstituted heterocycloalkyl, substituted or unsubstituted aryl, or substituted or unsubstituted heteroaryl;

R* is substituted or unsubstituted aryl, substituted or unsubstituted arylalkyl, substituted or unsubstituted heteroaryl, substituted or unsubstituted heteroarylalkyl, or substituted or unsubstituted vinyl;

with a proviso that when M is F, R* is not a member selected from:

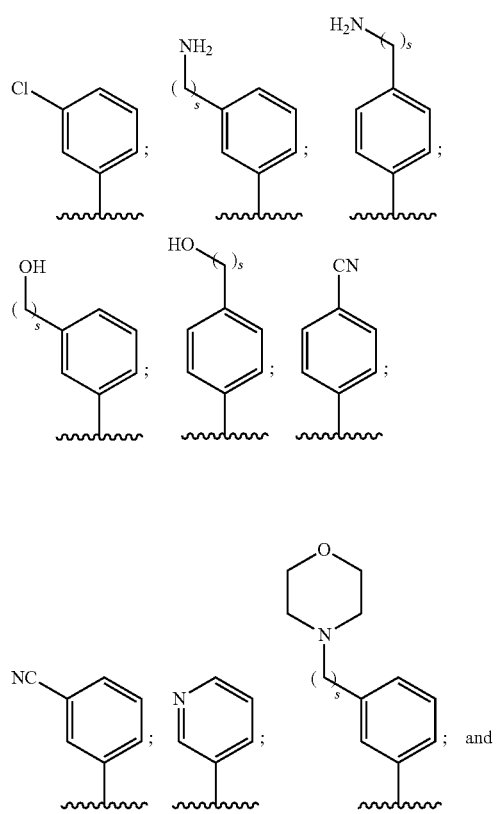

and with a proviso that when M is Cl, R* is not a member selected from:

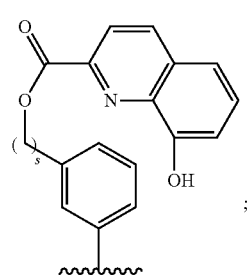

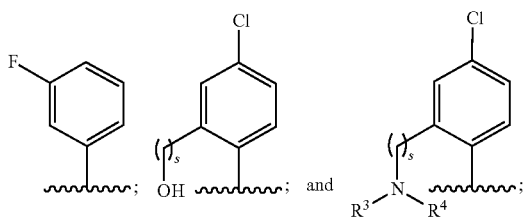

and with a proviso that when M is hydrogen, R* is not a member selected from:

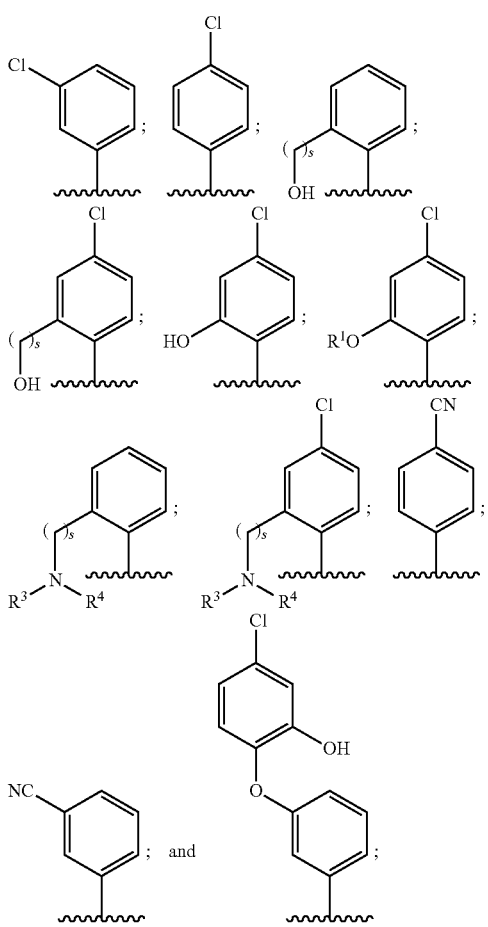

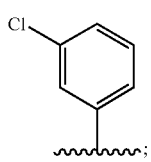

wherein s=1 or 2; and R³ and R⁴ are independently methyl or ethyl;

and with a provision that when M is OCH₃, R* is not a member selected from:

and with a provision that when M¹ is F, R* is not a member selected from:

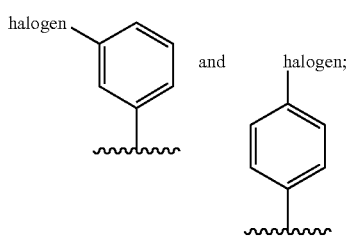

and pharmaceutically acceptable salts thereof.

In one embodiment of the method provided, the areas affected by the pathogens comprise vaginal yeast infections, athlete's foot, tinea, or combinations thereof. In another embodiment, the areas affected by the pathogens are selected from the group consisting of vaginal yeast infections, athlete's foot, tinea, or combinations thereof. In another embodiment, the pathogens comprise *Candida* spp. including *C. albicans, C. tropicalis, C. glabrata, C. krusei, C. parapsilosis, C. dubliniensis*, and *C. lusitaniae, Epidermophyton flocoosum, Trichiphyton rubrum, Trichophyton mentagrophytes*, or combinations thereof. In another embodiment, the pathogens are selected from the group consisting of *Candida albicans, C. tropicalis, C. glabrata, C. krusei, C. parapsilosis, C. dubliniensis, C. lusitaniae, Epidermophyton flocoosum, Trichiphyton rubrum, Trichophyton mentagrophytes*, or combinations thereof.

In another embodiment, the method provided further comprises impregnating, microencapsulating, or coating a material for releasing the volatile antimicrobial compound in a gaseous form. In a further embodiment, the matrix comprises a slow release mechanism. In another embodiment, the matrix comprises an absorbent material. In another embodiment, the matrix comprises a fabric. In a further embodiment, the absorbent material or fabric comprises materials made of cellulose, glass, polymer, nylon, or plastic fibers. In another embodiment, the volatile antimicrobial compound has a structure of

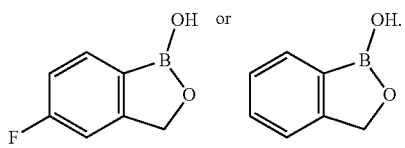 [SMILES: OB1OCc2cc(F)ccc21 ; "or" ; OB1OCc2ccccc21]

In another aspect, provided is a method of using a volatile antimicrobial compound against pathogens including human pathogens. The method comprises contacting areas infected by the pathogens with an atmosphere containing an effective amount of the volatile antimicrobial compound in gaseous form, the volatile antimicrobial compound having a structure of formula (IV):

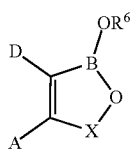

(IV)

wherein A and D together with the carbon atoms to which they are attached form a 5-, 6-, or 7-embered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, ($C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

wherein A, D and X are as defined herein except for boronophthalide;

and pharmaceutically acceptable salts thereof.

In one embodiment of the method provided, the areas affected by the pathogens comprise vaginal yeast infections, athlete's foot, tinea, or combinations thereof. In another embodiment, the areas affected by the pathogens are selected from the group consisting of vaginal yeast infections, athlete's foot, tinea, or combinations thereof. In another embodiment, the pathogens comprise *Candida* spp. including *C. albicans, C. tropicalis, C. glabrata, C. krusei, C. parapsilosis, C. dubliniensis*, and *C. lusitaniae, Epidermophyton flocoosum, Trichiphyton rubrum, Trichophyton mentagrophytes*, or combinations thereof. In another embodiment, the pathogens are selected from the group consisting of *Candida albicans, C. tropicalis, C. glabrata, C. krusei, C. parapsilosis, C. dubliniensis, C. lusitaniae, Epidermophyton flocoosum, Trichiphyton rubrum, Trichophyton mentagrophytes*, or combinations thereof.

In another embodiment, the method provided further comprises impregnating, microencapsulating, or coating a material for releasing the volatile antimicrobial compound in a gaseous form. In a further embodiment, the matrix comprises a slow release mechanism. In another embodiment, the matrix comprises an absorbent material. In another embodiment, the matrix comprises a fabric. In a further embodiment, the absorbent material or fabric comprises materials made of cellulose, glass, polymer, nylon, or plastic fibers. In another embodiment, the volatile antimicrobial compound has a structure of

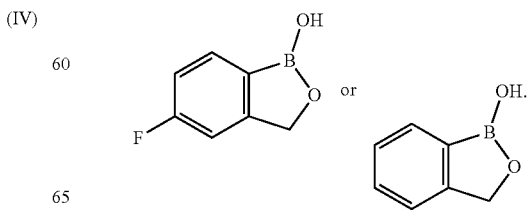

In another aspect, provided is a method of using a volatile antimicrobial compound against pathogens including human pathogens. The method comprises contacting areas infected by the pathogens with an atmosphere containing an effective amount of the volatile antimicrobial compound in gaseous form, the volatile antimicrobial compound having a structure of formula (VI):

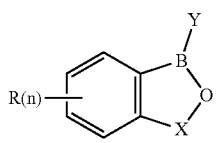
(VI)

wherein each R is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X=(CR_2)_m$ where m=1, 2, 3, or 4;

Y is alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

with a proviso that R is not aryloxy or heteroaryloxy when Y is hydroxyl;

and pharmaceutically acceptable salts thereof.

In one embodiment, the volatile antimicrobial compound has a structure of formula (VII):

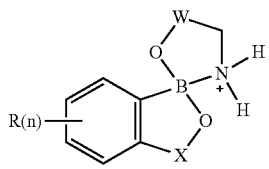
(VII)

wherein $W=(CH_2)_q$ where q is 1, 2, or 3.

In one embodiment of the method provided, the areas affected by the pathogens comprise vaginal yeast infections, athlete's foot, tinea, or combinations thereof. In another embodiment, the areas affected by the pathogens are selected from the group consisting of vaginal yeast infections, athlete's foot, tinea, or combinations thereof. In another embodiment, the pathogens comprise *Candida* spp. including *C. albicans, C. tropicalis, C. glabrata, C. krusei, C. parapsilosis, C. dubliniensis,* and *C. lusitaniae, Epidermophyton flocoosum, Trichiphyton rubrum, Trichophyton mentagrophytes,* or combinations thereof. In another embodiment, the pathogens are selected from the group consisting of *Candida albicans, C. tropicalis, C. glabrata, C. krusei, C. parapsilosis, C. dubliniensis, C. lusitaniae, Epidermophyton flocoosum, Trichiphyton rubrum, Trichophyton mentagrophytes,* or combinations thereof.

In another embodiment, the method provided further comprises impregnating, microencapsulating, or coating a material for releasing the volatile antimicrobial compound in a gaseous form. In a further embodiment, the matrix comprises a slow release mechanism. In another embodiment, the matrix comprises an absorbent material. In another embodiment, the matrix comprises a fabric. In a further embodiment, the absorbent material or fabric comprises materials made of cellulose, glass, polymer, nylon, or plastic fibers. In another embodiment, the volatile antimicrobial compound has a structure of

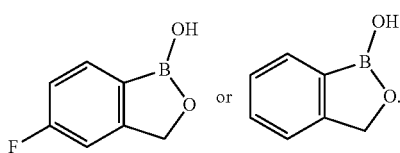 [SMILES: OB1OCc2cc(F)ccc21 ; OB1OCc2ccccc21]

In another aspect, provided is a method of using a volatile antimicrobial compound against pathogens including human pathogens. The method comprises contacting areas infected by the pathogens with an atmosphere containing an effective amount of the volatile antimicrobial compound in gaseous form, the volatile antimicrobial compound having a structure of formula (VIII):

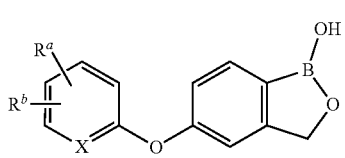
(VIII)

wherein $R^a$ is CN, $C(O)NR^9R^{10}$, or $C(O)OR^{11}$ wherein $R^{11}$ is hydrogen, substituted alkyl, or unsubstituted alkyl, X is N, CH and $CR^b$;

$R^b$ is halogen, substituted or unsubstituted alkyl, $C(O)R^{12}$, $C(O)OR^{12}$, $OR^{12}$, $NR^{12}R^{13}$, wherein $R^9$, $R^{10}$, $R^{12}$, and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

with a proviso that $R^9$ and $R^{10}$, together with the atoms to which they are attached, are optionally combined to form a 4- to 8-membered substituted or unsubstituted heterocycloalkyl ring;

and with a proviso that $R^{12}$ and $R^{13}$, together with the atoms to which they are attached, are optionally combined to form a 4- to 8-membered substituted or unsubstituted heterocycloalkyl ring;

and pharmaceutically acceptable salts thereof.

In one embodiment of the method provided, the areas affected by the pathogens comprise vaginal yeast infections, athlete's foot, tinea, or combinations thereof. In another embodiment, the areas affected by the pathogens are selected from the group consisting of vaginal yeast infections, athlete's foot, tinea, or combinations thereof. In another embodiment, the pathogens comprise *Candida* spp. including *C. albicans, C. tropicalis, C. glabrata, C. krusei, C. parapsilosis, C. dubliniensis*, and *C. lusitaniae, Epidermophyton flocoosum, Trichiphyton rubrum, Trichophyton mentagrophytes*, or combinations thereof. In another embodiment, the pathogens are selected from the group consisting of *Candida albicans, C. tropicalis, C. glabrata, C. krusei, C. parapsilosis, C. dubliniensis, C. lusitaniae, Epidermophyton flocoosum, Trichiphyton rubrum, Trichophyton mentagrophytes*, or combinations thereof.

In another embodiment, the method provided further comprises impregnating, microencapsulating, or coating a material for releasing the volatile antimicrobial compound in a gaseous form. In a further embodiment, the matrix comprises a slow release mechanism. In another embodiment, the matrix comprises an absorbent material. In another embodiment, the matrix comprises a fabric. In a further embodiment, the absorbent material or fabric comprises materials made of cellulose, glass, polymer, nylon, or plastic fibers. In another embodiment, the volatile antimicrobial compound has a structure of

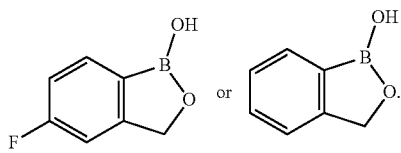

In another aspect, provided is a method of using a volatile antimicrobial compound against pathogens including human pathogens. The method comprises contacting areas infected by the pathogens with an atmosphere containing an effective amount of the volatile antimicrobial compound in gaseous form, the volatile antimicrobial compound having a structure of formula (A):

$$R^A\text{-}L^A\text{-}G\text{-}L^B\text{-}R^B \quad (A),$$

wherein each of $R^A$ and $R^B$ is independently derived from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof;

the -$L^A$-G-$L^B$- portion of formula (A) is derived from a diol or diamine compound; the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof; and the diamine compound is 1,2-ethylene diamine; 1,3-propylene diamine; or combinations thereof; G is a substituted or unsubstituted $C_{1-8}$-alkylene;

and pharmaceutically acceptable salts thereof.

In one embodiment, the compound is volatile. In another embodiment, the compound is a fungicide. In another embodiment, G is selected from —CH$_2$—, —CH$_2$—CH$_2$—, —CH$_2$—CH$_2$—CH$_2$—, —CH(CH$_3$)—CH$_2$—, —C(CH$_3$)$_2$—C(CH$_3$)$_2$—, and —CH$_2$—C(CH$_3$)$_2$—CH$_2$—. In another embodiment, G is selected from —CH$_2$—, —CH$_2$—CH$_2$—, and —CH$_2$—CH$_2$—CH$_2$—.

In another embodiment, each of $R^A$ and $R^B$ is independently

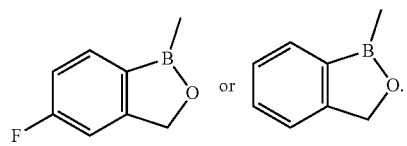

In another embodiment, the compound has the structure of

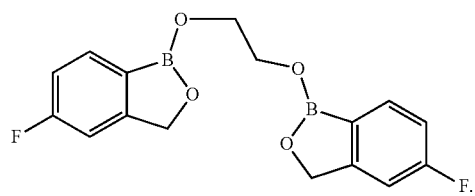 [SMILES: Fc1ccc2c(c1)COB2OCCOB1OCc2cc(F)ccc21]

In one embodiment of the method provided, the areas affected by the pathogens comprise vaginal yeast infections, athlete's foot, tinea, or combinations thereof. In another embodiment, the areas affected by the pathogens are selected from the group consisting of vaginal yeast infections, athlete's foot, tinea, or combinations thereof. In another embodiment, the pathogens comprise *Candida* spp. including *C. albicans, C. tropicalis, C. glabrata, C. krusei, C. parapsilosis, C. dubliniensis*, and *C. lusitaniae, Epidermophyton flocoosum, Trichiphyton rubrum, Trichophyton mentagrophytes*, or combinations thereof. In another embodiment, the pathogens are selected from the group consisting of *Candida albicans, C. tropicalis, C. glabrata, C. krusei, C. parapsilosis, C. dubliniensis, C. lusitaniae, Epidermophyton flocoosum, Trichiphyton rubrum, Trichophyton mentagrophytes*, or combinations thereof.

In another embodiment, the method provided further comprises impregnating, microencapsulating, or coating a material for releasing the volatile antimicrobial compound in a gaseous form. In a further embodiment, the matrix comprises a slow release mechanism. In another embodiment, the matrix comprises an absorbent material. In another embodiment, the matrix comprises a fabric. In a further embodiment, the absorbent material or fabric comprises materials made of cellulose, glass, polymer, nylon, or plastic fibers.

In one aspect, provided is a method of using a volatile antimicrobial compound against pathogens including human pathogens. The method comprises:
(a) mixing a volatile antimicrobial compound with an organic solvent;
(b) heating the mixture from step (a) to evaporate the organic solvent and render the volatile antimicrobial compound into its gaseous form; and
(c) contacting areas infected by the pathogens with an atmosphere containing an effective amount of the volatile antimicrobial compound in gaseous form at a temperature between 1° C. and 50° C.;
wherein the volatile antimicrobial compound having a structure of formula (I), (II), (III), (IV), (VI), (VII), (VIII), (IX), (X), (XI), (XII), (XIII), (A), (A1), or (A2) provided herein.

In one embodiment of the method provided, the areas affected by the pathogens comprise vaginal yeast infections, athlete's foot, tinea, or combinations thereof. In another embodiment, the areas affected by the pathogens are selected from the group consisting of vaginal yeast infections, athlete's foot, tinea, or combinations thereof. In another embodiment, the pathogens comprise *Candida* spp. including *C. albicans, C. tropicalis, C. glabrata, C. krusei, C. parapsilosis, C. dubliniensis*, and *C. lusitaniae, Epidermophyton flocoosum, Trichiphyton rubrum, Trichophyton mentagrophytes*, or combinations thereof. In another embodiment, the pathogens are selected from the group consisting of *Candida albicans, C. tropicalis, C. glabrata, C. krusei, C. parapsilosis, C. dubliniensis, C. lusitaniae, Epidermophyton flocoosum, Trichiphyton rubrum, Trichophyton mentagrophytes*, or combinations thereof.

In another embodiment, the heating step is performed at a temperature between 30° C. and 300° C.; between 35° C. and 200° C.; between 35° C. and 150° C.; between 30° C. and 50° C.; or between 35° C. and 45° C.

In another embodiment, the contacting step is performed at a temperature between 10° C. and 50° C.; between 1° C. and 10° C.; between 20° C. and 50° C.; between 2° C. and 30° C.; or between 35° C. and 45° C. In another embodiment, the organic solvent comprises acetone or ethanol. In another embodiment, the volatile antimicrobial compound remains in its gaseous form for two days, seven days, ten days, fourteen days, thirty days, forty days, or sixty days.

DETAILED DESCRIPTION OF THE INVENTION

Provided are methods and new uses of volatile compounds based on a discovery that benzoxaborole compounds have volatility at room temperature, a cold storage temperature (for example 1° C. to 10° C.), or a human body temperature. Delivery of the active ingredient may depend on impregnating a matrix which will release the active ingredient in a volatile form slowly over time in the vicinity of the infected area. Examples may include the release of the benzoxaborole active ingredient from bed liners of shoes and shoe inserts, cotton, nylon, or material blend fabrics utilized in socks, from an insert that fits between the toes and sock, a bandage-like system with wraps and adhesives to secure the matrix for athlete's foot. For vaginal yeast infections the benzoxaborole active ingredient may be imbedded into panty liner pads or within the cotton, nylon, or material blend fabric utilized in underwear for vaginal yeast infections. Matrixes in both cases may be made of all sorts of materials from aramid fiber, cellulosic fiber, cotton fiber, fiberglass fiber, silica fiber, coated or impregnated polymers, to PTFE-, vinyl-, acrylic-, silicone-coated fibers, to plastic or nylon materials and fibers.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg, *Advanced Organic Chemistry* 4th Ed., Vols. A (2000) and B (2001), Plenum Press, New York, N.Y.

As used herein, the phrase "moiety" refers to a specific segment or functional group of a molecule. Chemical moieties are often recognized chemical entities embedded in or appended to a molecule.

As used herein, the phrases "heteroatom" and "hetero-" refer to atoms other than carbon (C) and hydrogen (H). Examples of heteroatoms include oxygen (O), nitrogen (N), sulfur (S), silicon (Si), germanium (Ge), aluminum (Al) and boron (B).

As used herein, the phrases "halo" and "halogen" are interchangeable and refer to fluoro (—F), chloro (—Cl), bromo (—Br), and iodo (—I).

As used herein, the phrase "alkyl" refers to an unsubstituted or substituted, hydrocarbon group and can include straight, branched, cyclic, saturated and/or unsaturated features. Although the alkyl moiety may be an "unsaturated alkyl" moiety, which means that it contains at least one alkene or alkyne moiety, typically, the alkyl moiety is a "saturated alkyl" group, which means that it does not contain any alkene or alkyne moieties. Likewise, although the alkyl moiety may be cyclic, the alkyl moiety typically is acyclic group. Thus, in some embodiments, "alkyl" refers to an optionally substituted straight-chain, or optionally substituted branched-chain saturated hydrocarbon monoradical having from about one to about thirty carbon atoms in some embodiments, from about one to about fifteen carbon atoms in some embodiments, and from about one to about six carbon atoms in further embodiments. Examples of saturated alkyl radicals include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, tert-butyl, n-pentyl, isopentyl, neopentyl, and n-hexyl, and longer alkyl groups, such as heptyl, and octyl. It should be noted that whenever it appears herein, a numerical range such as "1 to 6" refers to each integer in the given range; e.g., "1 to 6 carbon atoms" or "$C_1$-6" or "$C_1$-$C_6$" means that the alkyl group may consist of 1 carbon atom, 2 carbon atoms, 3 carbon atoms, 4 carbon atoms, 5 carbon atoms, and/or 6 carbon atoms, although the present definition also covers the occurrence of the term "alkyl" where no numerical range is designated.

As used herein, the phrase "substituted alkyl" refers to an alkyl group, as defined herein, in which one or more (up to about five, preferably up to about three) hydrogen atoms is replaced by a substituent independently selected from the substituent group defined herein.

As used herein, the phrases "substituents" and "substituted" refer to groups which may be used to replace another group on a molecule. Such groups are known to those of skill in the chemical arts and may include, without limitation, one or more of the following independently selected groups, or designated subsets thereof: halogen, —CN, —OH, —$NO_2$, —$N_3$, =O, =S, =NH, —$SO_2$, —$NH_2$, —COOH, nitroalkyl, amino, including mono- and di-substituted amino groups, cyanato, isocyanato, thiocyanato, isothiocyanato, guanidinyl, O-carbamyl, N-carbamyl, thiocarbamyl, uryl, isouryl, thiouryl, isothiouryl, mercapto, sulfanyl, sulfinyl, sulfonyl, sulfonamidyl, phosphonyl, phosphatidyl, phosphoramidyl, dialkylamino, diarylamino, diarylalkylamino; and the protected compounds thereof. The protecting groups that may form the protected compounds of the above substituents are known to those of skill in the art and may be found in references such as Greene and Wuts, *Protective Groups in Organic Synthesis,* 3rd ed.; John Wiley & Sons, New York, N.Y. (1999) and Kocienski, *Protective Groups*; Thieme Verlag, New York, N.Y. (1994) which are incorporated herein by reference in their entirety.

As used herein, the phrase "alkoxy" refers to the group —O-alkyl, where alkyl is as defined herein. In one embodiment, alkoxy groups include, e.g., methoxy, ethoxy, n-propoxy, isopropoxy, n-butoxy, tert-butoxy, sec-butoxy, n-pentoxy, n-hexoxy, 1,2-dimethylbutoxy, and the like. The alkoxy can be unsubstituted or substituted.

As used herein, the phrases "cyclic" and "membered ring" refer to any cyclic structure, including alicyclic, heterocyclic, aromatic, heteroaromatic and polycyclic fused or non-fused ring systems as described herein. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

As used herein, the phrase "aromatic" refers to a cyclic or polycyclic moiety having a conjugated unsaturated (4n+2)π electron system (where n is a positive integer), sometimes referred to as a delocalized it electron system.

As used herein, the phrase "aryl" refers to an optionally substituted, aromatic, cyclic, hydrocarbon monoradical of from six to about twenty ring atoms, preferably from six to about ten carbon atoms and includes fused (or condensed) and non-fused aromatic rings. A fused aromatic ring radical contains from two to four fused rings where the ring of attachment is an aromatic ring, and the other individual rings within the fused ring may be cycloalkyl, cycloalkenyl, cycloalkynyl, heterocycloalkyl, heterocycloalkenyl, heterocycloalkynyl, aromatic, heteroaromatic or any combination thereof. A non-limiting example of a single ring aryl group includes phenyl; a fused ring aryl group includes naphthyl, anthryl, azulenyl; and a non-fused bi-aryl group includes biphenyl.

As used herein, the phrase "substituted aryl" refers to an aryl group, as defined herein, in which one or more (up to about five, preferably up to about three) hydrogen atoms is replaced by a substituent independently selected from the group defined herein, (except as otherwise constrained by the definition for the aryl substituent).

As used herein, the phrase "heteroaryl" refers to an optionally substituted, aromatic, cyclic monoradical containing from about five to about twenty skeletal ring atoms, preferably from five to about ten ring atoms and includes fused (or condensed) and non-fused aromatic rings, and which have one or more (one to ten, preferably about one to about four) ring atoms selected from an atom other than carbon (i.e., a heteroatom) such as, for example, oxygen, nitrogen, sulfur, selenium, phosphorus or combinations thereof. The term heteroaryl includes optionally substituted fused and non-fused heteroaryl radicals having at least one heteroatom. A fused heteroaryl radical may contain from two to four fused rings where the ring of attachment is a heteroaromatic ring and the other individual rings within the fused ring system may be alicyclic, heterocyclic, aromatic, heteroaromatic or any combination thereof. The term heteroaryl also includes fused and non-fused heteroaryls having from five to about twelve skeletal ring atoms, as well as those having from five to about ten skeletal ring atoms. Examples of heteroaryl groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiadiazolyl, benzothiazolyl, benzo[b]thienyl, benzothiophenyl, benzothiopyranyl, benzotriazolyl, benzoxazolyl, carbazolyl, carbolinyl, chromenyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathiynyl, thianthrenyl, phenathridinyl, phenathrolinyl, phthalazinyl, pteridinyl, purinyl, puteridinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3)- and (1,2,4)-triazolyl and the like, and their oxides where appropriate, such as for example pyridyl-N-oxide.

As used herein, the phrase "substituted heteroaryl" refers to a heteroaryl group, as defined herein, in which one or more (up to about five, preferably up to about three) hydrogen atoms is replaced by a substituent independently selected from the group defined herein.

As used herein, the phrase "leaving group" refers to a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like. In some embodiments, a leaving group can be HC(O)—COOH or RC(O)—COOH, wherein R is a $C_1$-$C_6$ alkyl or substituted $C_1$-$C_6$ alkyl.

The compounds of the invention as described herein may be synthesized using standard synthetic techniques known to those of skill in the art or using methods known in the art in combination with methods described herein. The starting materials used for the synthesis of the compounds of the invention as described herein, can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, *Advanced Organic Chemistry* 4th Ed. (1992) John Wiley & Sons, New York, N.Y.; Carey and Sundberg, *Advanced Organic Chemistry* 4th Ed., Vols. A (2000) and B (2001) Plenum Press, New York, N.Y. and Greene and Wuts, *Protective Groups in Organic Synthesis*, 3rd Ed. (1999) John Wiley & Sons, New York, N.Y., (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulae as provided herein. For example, the compounds described herein can be modified using various electrophiles or nucleophiles to form new functional groups or substituents.

In some embodiments, the volatile antimicrobial compound of the invention has a structure of formula (I), (II), or (III):

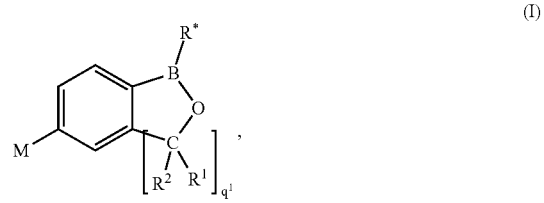

-continued

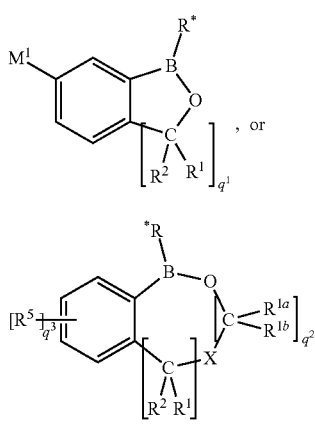
(II)

, or

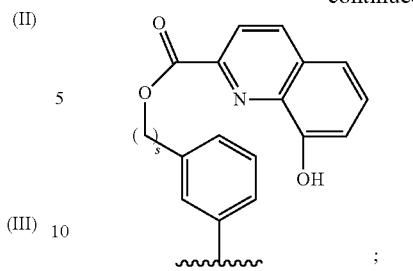
(III)

wherein q1 and q2 are independently 1, 2, or 3;
q3=0, 1, 2, 3, or 4;
M is hydrogen, halogen, —OCH$_3$, or —CH$_2$—O—CH$_2$—O—CH$_3$;
M$^1$ is halogen, —CH$_2$OH, or —OCH$_3$;
X is O, S, or NR$^{1c}$, wherein R$^{1c}$ is hydrogen, substituted alkyl, or unsubstituted alkyl;
R$^1$, R$^{1a}$, R$^{1b}$, R$^2$, and R$^5$ are independently hydrogen, OH, NH$_2$, SH, CN, NO$_2$, SO$_2$, OSO$_2$OH, OSO$_2$NH$_2$, substituted or unsubstituted cycloalkyl, substituted or unsubstituted heterocycloalkyl, substituted or unsubstituted aryl, or substituted or unsubstituted heteroaryl;
R* is substituted or unsubstituted aryl, substituted or unsubstituted arylalkyl, substituted or unsubstituted heteroaryl, substituted or unsubstituted heteroarylalkyl, or substituted or unsubstituted vinyl;
with a proviso that when M is F, R* is not a member selected from:

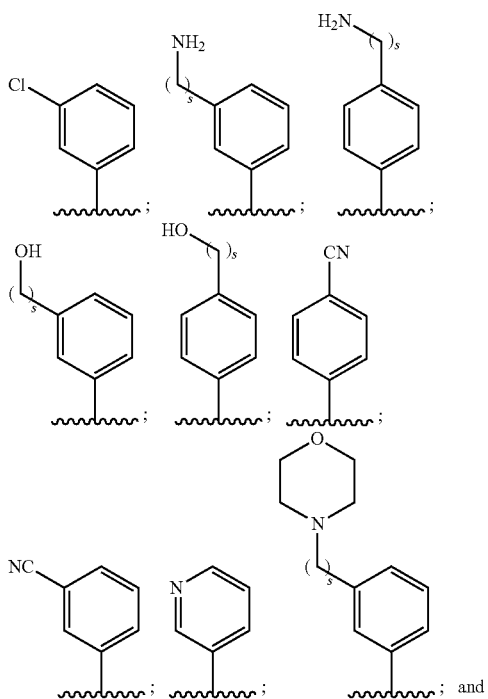

and with a proviso that when M is Cl, R* is not a member selected from:

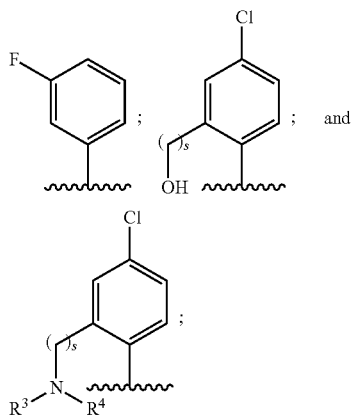

and with a proviso that when M is hydrogen, R* is not a member selected from:

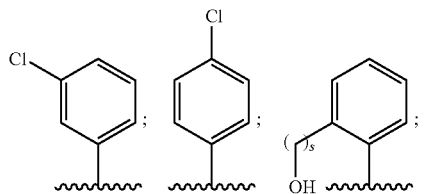

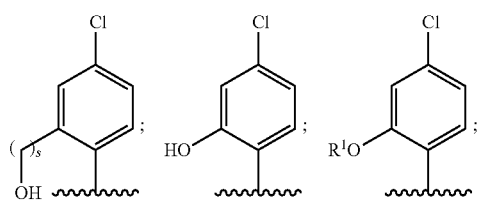

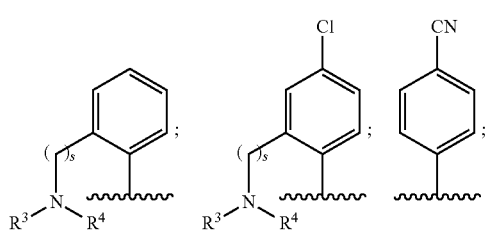

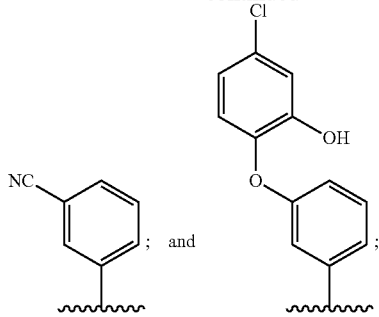
; and wherein s=1 or 2; and $R^3$ and $R^4$ are independently methyl or ethyl;

and with a provision that when M is $OCH_3$, R* is not a member selected from:

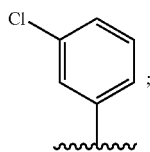
;

and with a provision that when $M^1$ is F, R* is not a member selected from:

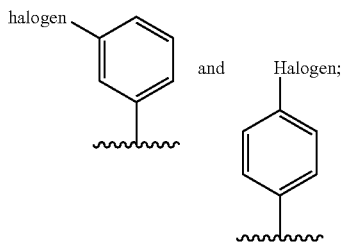

and pharmaceutically acceptable salts thereof.

In one embodiment, the R* has a structure selected from:

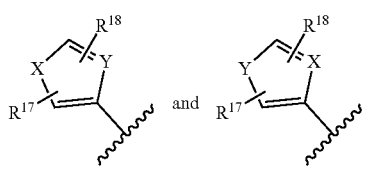

wherein X is a member selected from CH=CH, N=CH, $NR^{14}$, O and S;

wherein $R^{14}$ is a member selected from H, substituted or unsubstituted alkyl, substituted or unsubstituted aryl and substituted or unsubstituted arylalkyl;

Y is a member selected from CH and N;

$R^{17}$ and $R^{18}$ are members independently selected from H, substituted or unsubstituted alkyl, substituted or unsubstituted aryl, substituted or unsubstituted arylalkyl, $(CH_2)_v OH$, $(CH_2)_w NR^{15}R^{16}$, $CO_2H$, $CO_2$-alkyl, $CONH_2$, S-alkyl, S-aryl, SO-alkyl, SO-aryl, $SO_2$-alkyl, $SO_2$-aryl, $SO_2H$, $SCF_2$, CN, halogen, $CF_3$ and $NO_2$;

wherein $R^{15}$ and $R^{16}$ are members independently selected from hydrogen, substituted or unsubstituted alkyl and substituted or unsubstituted alkanoyl;

v=1, 2, or 3; and
w=0, 1, 2, or 3.

In another embodiment, the R* has the following structure:

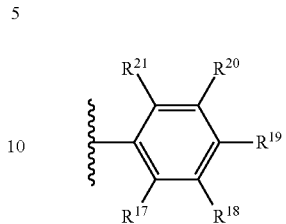

wherein $R^{17}$, $R^{18}$, $R^{19}$, $R^{20}$, and $R^{21}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_t OH$, $CO_2H$, $CO_2$— alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_2H$, $SCF_3$, CN, halogen, $CF_3$, $NO_2$, $(CH_2)_u NR^{22}R^{23}$, $SO_2NH_2$, $OCH_2CH_2NH_2$, $OCH_2CH_2NH$-alkyl and $OCH_2CH_2N(alkyl)_2$;

wherein t=1, 2 or 3;
u=0, 1, or 2;

$R^{22}$ and $R^{23}$ are independently selected from H, substituted or unsubstituted alkyl, and substituted or unsubstituted alkanoyl.

In another embodiment, the R* has the following structure:

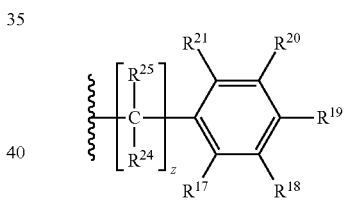

wherein $R^{17}$, $R^{18}$, $R^{19}$, $R^{20}$, and $R^{21}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_t OH$, $CO_2H$, $CO_2$— alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_2H$, $SCF_3$, CN, halogen, $CF_3$, $NO_2$, $(CH_2)_u NR^{22}R^{23}$, $SO_2NH_2$, $OCH_2CH_2NH_2$, $OCH_2CH_2NH$-alkyl and $OCH_2CH_2N(alkyl)_2$;

wherein t=1, 2 or 3;
u=0, 1, or 2;

$R^{22}$ and $R^{23}$ are independently selected from H, substituted or unsubstituted alkyl, and substituted or unsubstituted alkanoyl;

$R^{24}$ and $R^{25}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)$, OH, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$;

Z=1, 2, 3, 4, 5, or 6.

Additional antimicrobial compounds are also disclosed previously in U.S. Pat. No. 8,106,031, and International Patent Application WO 2007/131072A2, the contents of which are hereby incorporated by reference in their entireties.

In some embodiments, the volatile antimicrobial compound of the invention has the structure of formula (IV):

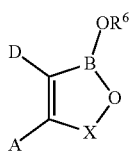

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

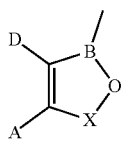

(V)

wherein A, D and X are as defined herein before except for boronophthalide;

and pharmaceutically acceptable salts thereof.

In one embodiment, the volatile antimicrobial compound of the invention has the structure of formula (IX):

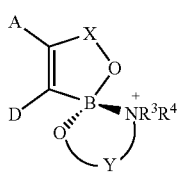

(IX)

wherein A, D, and X are defined as above;

Y is a divalent alkylene linking group containing up to 18 carbon atoms or a divalent alkylene linking group containing up to 18 carbon atoms which is substituted by phenyl, $C_1$-$C_6$-alkoxy, $C_1$-$C_6$-alkylthio; carbonyl alkylene amino; and $R^3$ and $R^4$ are each, independently, hydrogen, $C_1$-$C_{18}$-alkyl or phenyl or $R^3$ together with Y or part of Y forms a 5-, 6- or 7-membered ring containing the nitrogen atom.

In another embodiment, the volatile antimicrobial compound of the invention has the structure of formula (X):

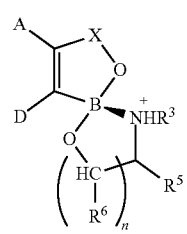

(X)

wherein A, D, and X are defined as above;

n is 1, 2, or 3;

$R^3$ is hydrogen, $C_1$-$C_{18}$-alkyl or phenyl; and $R^5$ and $R^6$ are each, independently, hydrogen, alkyl containing up to a total of 16 carbon atoms or phenyl.

Additional antimicrobial compounds are also disclosed previously in U.S. Pat. No. 5,880,188, the content of which is hereby incorporated by reference in its entirety.

In another aspect, the volatile antimicrobial compound of the invention has the structure of formula (VI):

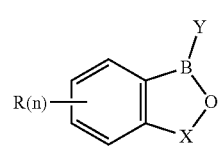

(VI)

wherein each R is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

X=$(CR_2)_m$ where m=1, 2, 3, or 4;

Y is alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

with a proviso that R is not aryloxy or heteroaryloxy when Y is hydroxyl;

and pharmaceutically acceptable salts thereof.

In one embodiment, the volatile antimicrobial compound has a structure of formula (VII):

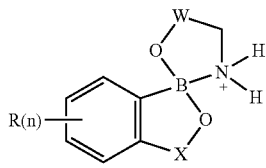
(VII)

wherein W=(CH$_2$)$_q$ where q is 1, 2, or 3.

In another embodiment, the volatile antimicrobial compound has a structure of

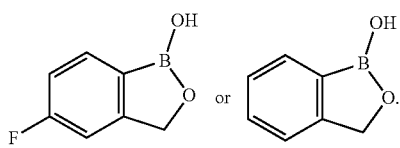 [SMILES: OB1OCc2cc(F)ccc21 ; OB1OCc2ccccc21]

In another embodiment, the volatile antimicrobial compound of the invention has the structure of formula (VIII):

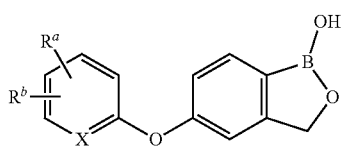
(VIII)

wherein R$^a$ is CN, C(O)NR$^9$R$^{10}$, or C(O)OR$^{11}$ wherein R$^{11}$ is hydrogen, substituted alkyl, or unsubstituted alkyl,
X is N, CH and CR$^b$;
R$^b$ is halogen, substituted or unsubstituted alkyl, C(O)R$^{12}$, C(O)OR$^{12}$, OR$^{12}$, NR$^{12}$R$^{13}$, wherein R$^9$, R$^{10}$, R$^{12}$, and R$^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
with a proviso that R$^9$ and R$^{10}$, together with the atoms to which they are attached, are optionally combined to form a 4- to 8-membered substituted or unsubstituted heterocycloalkyl ring;
and with a proviso that R$^{12}$ and R$^{13}$, together with the atoms to which they are attached, are optionally combined to form a 4- to 8-membered substituted or unsubstituted heterocycloalkyl ring;
and pharmaceutically acceptable salts thereof.

In one embodiment, the volatile antimicrobial compound of the invention has the structure of formula (XI):

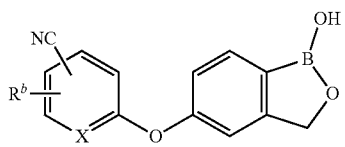
(XI)

In another embodiment, the volatile antimicrobial compound of the invention is selected from:

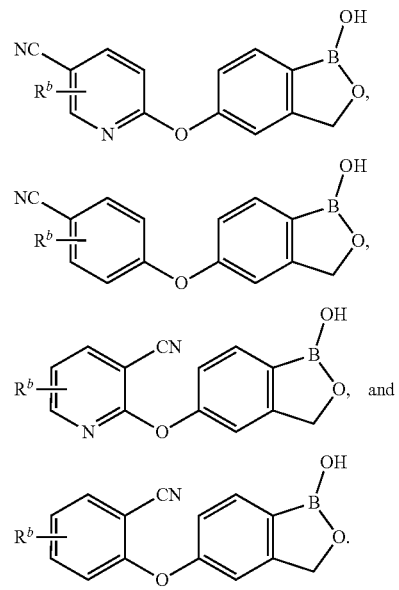

In another embodiment, the volatile antimicrobial compound of the invention is selected from:

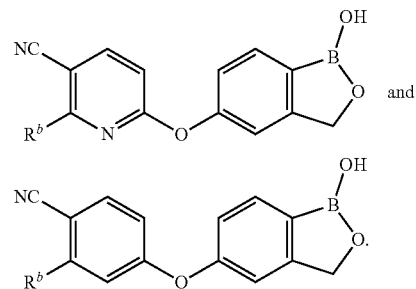

In another embodiment, the volatile antimicrobial compound of the invention is selected from:

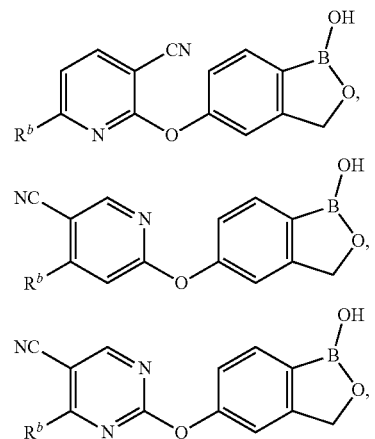

-continued

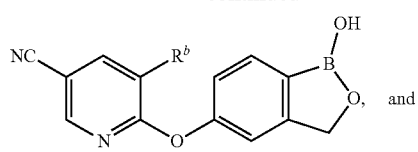

and

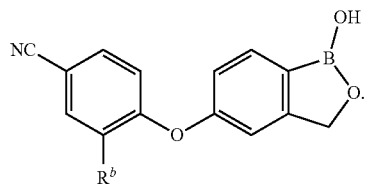

In one embodiment, the volatile antimicrobial compound of the invention has the structure of formula (XII):

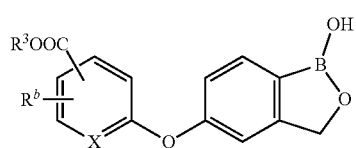
(XII)

In another embodiment, the volatile antimicrobial compound of the invention is selected from:

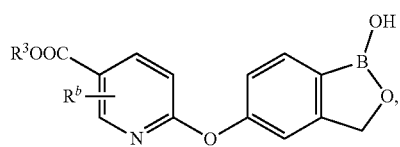

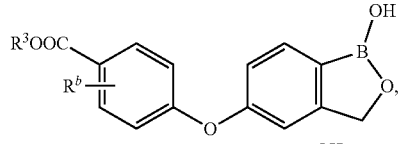

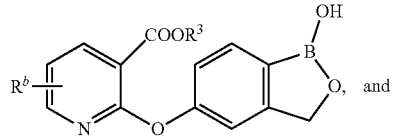

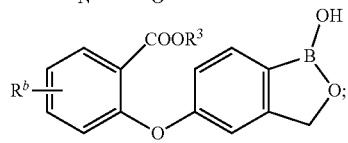

wherein $R^3$ is hydrogen, substituted or unsubstituted alkyl, or substituted or unsubstituted heteroalkyl.

In another embodiment, the volatile antimicrobial compound of the invention is selected from:

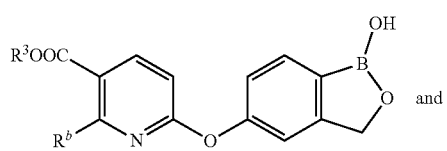 and

-continued

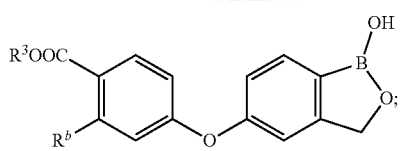

wherein $R^3$ is hydrogen, substituted or unsubstituted alkyl, or substituted or unsubstituted heteroalkyl.

In another embodiment, the volatile antimicrobial compound of the invention is selected from:

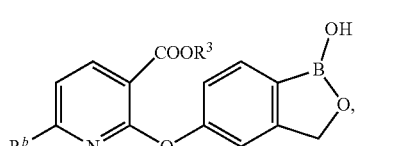

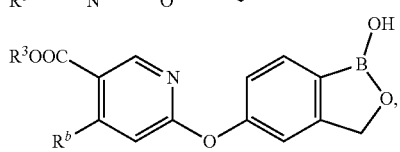

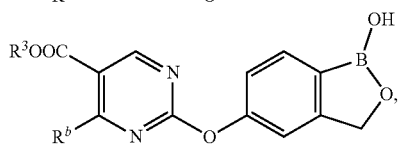

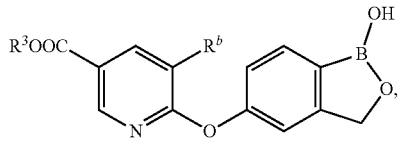 and

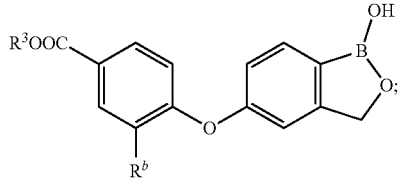

wherein $R^3$ is hydrogen, substituted or unsubstituted alkyl, or substituted or unsubstituted heteroalkyl.

In one embodiment, the volatile antimicrobial compound of the invention has the structure of formula (XIII):

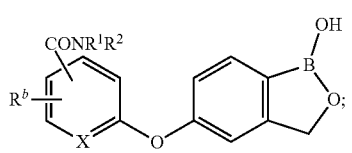
(XIII)

wherein each of $R^1$ and $R^2$ is independently hydrogen, substituted or unsubstituted alkyl, or substituted or unsubstituted heteroalkyl.

In another embodiment, the volatile antimicrobial compound of the invention is selected from:

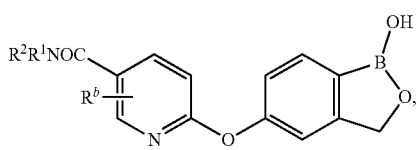

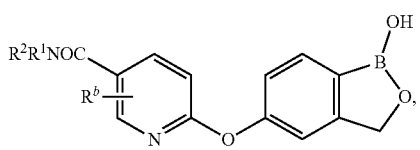

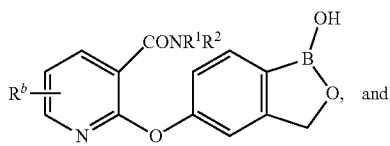

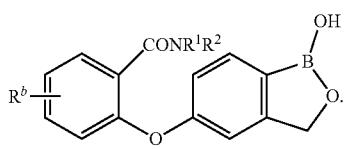

In another embodiment, the volatile antimicrobial compound of the invention is selected from:

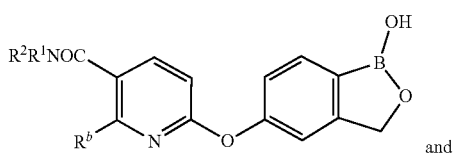

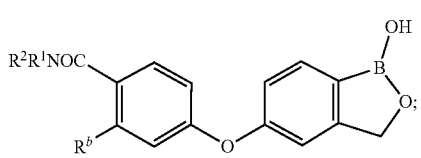

wherein each of R¹ and R² is independently hydrogen, substituted or unsubstituted alkyl, or substituted or unsubstituted heteroalkyl.

In another embodiment, the volatile antimicrobial compound of the invention is selected from:

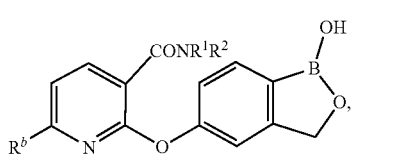

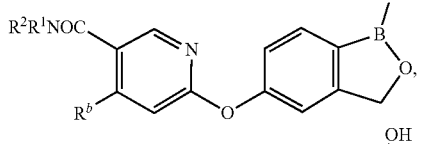

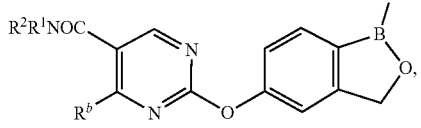

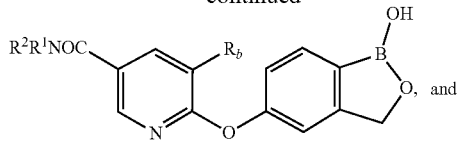

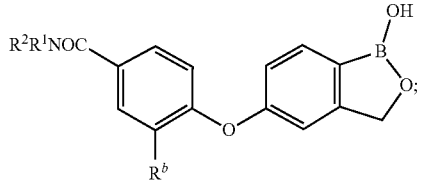

wherein each of $R^1$ and $R^2$ is independently hydrogen, substituted or unsubstituted alkyl, or substituted or unsubstituted heteroalkyl.

In one embodiment, $R^b$ is selected from fluorine and chlorine. In another embodiment, $R^b$ is selected from $OR^{26}$ and $NR^{27}R^{28}$. In another embodiment when $R^b$ is $OR^{26}$, $R^{26}$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $OR^{26}$, $R^{26}$ is selected from H, substituted or unsubstituted alkyl, substituted or unsubstituted heteroalkyl and substituted or unsubstituted cycloalkyl. In another embodiment when $R^b$ is $OR^{26}$, $R^{26}$ is unsubstituted $C_1$-$C_6$ alkyl. In another embodiment when $R^b$ is $OR^{26}$, $R^{26}$ is unsubstituted cycloalkyl. In another embodiment when $R^b$ is $OR^{26}$, $R^{26}$ is alkyl, substituted with a member selected from substituted or unsubstituted $C_1$-$C_6$ alkoxy. In another embodiment when $R^b$ is $OR^{26}$, $R^{26}$ is alkyl, substituted with at least one halogen. In another embodiment when $R^b$ is $OR^{26}$, $R^{26}$ is alkyl, substituted with at least one oxo moiety.

In another embodiment when $R^b$ is $OR^{26}$, $R^{26}$ is a member selected from —CH₃, —CH₂CH₃, —(CH₂)₂CH₃, —CH(CH₃)₂, —CH₂CF₃, —CH₂CHF₂, —CH₂CH₂(OH), —CH₂CH₂(OCH₃), —CH₂CH₂(OC(CH₃)₃), —C(O)CH₃, —CH₂CH₂OC(O)CH₃, —CH₂C(O)OCH₂CH₃, —CH₂C(O)OC(CH₃)₃, —(CH₂)₃C(O)CH₃, —CH₂C(O)OC(CH₃)₃, cyclopentyl, cyclohexyl,

, and

.

In another embodiment when $R^b$ is $NR^{27}R^{28}$, $R^{27}$ and $R^{28}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $NR^{27}R^{28}$, $R^{27}$ is H or unsubstituted alkyl; and $R^{28}$ is unsubstituted alkyl or alkyl substituted with a member selected from hydroxyl, phenyl, unsubstituted alkoxy and alkoxy substituted with a phenyl. In a further embodiment when $R^b$ is $NR^{27}R^{28}$, $R^{27}$ is H or CH₃.

In another embodiment when $R^b$ is $NR^{27}R^{28}$, $R^{27}$ and $R^{28}$ are independently selected from substituted or unsubstituted alkyl. In another embodiment when $R^b$ is $NR^{27}R^{28}$, $R^{27}$ is unsubstituted alkyl; and $R^{28}$ is substituted or unsubstituted alkyl. In another embodiment when $R^b$ is $NR^{27}R^{28}$, $R^{27}$ is unsubstituted alkyl; and $R^{28}$ is alkyl, substituted with a member selected from substituted or unsubstituted alkoxy and hydroxyl. In another embodiment when $R^b$ is $NR^{27}R^{28}$, $R^{27}$ is unsubstituted alkyl; and $R^{28}$ is alkyl, substituted with unsubstituted alkoxy. In another embodiment when $R^b$ is $NR^{27}R^{28}$, $R^{27}$ is unsubstituted alkyl; and $R^{28}$ is alkyl, substituted with alkoxy, substituted with phenyl. In another embodiment when $R^b$ is $NR^{27}R^{28}$, $R^{27}$ is unsubstituted alkyl; and $R^{28}$ is alkyl, substituted with unsubstituted alkoxy. In another embodiment when $R^b$ is $NR^{27}R^{28}$, $R^{27}$ and $R^{2s}$ together with the nitrogen to which they are attached, are combined to form a 4- to 8-membered substituted or unsubstituted heterocycloalkyl ring. In another embodiment when $R^b$ is $NR^{27}R^{28}$, $R^{27}$ and $R^{28}$ together with the nitrogen to which they are attached, are combined to form a 5- or 6-membered substituted or unsubstituted heterocycloalkyl ring.

In another embodiment, $R^b$ is selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph)$, $NH(CH_2Ph)$, $NH(C(CH_3)_3)$ and $NH(CH_2CH_2OH)$. In another embodiment, $R^b$ is selected from

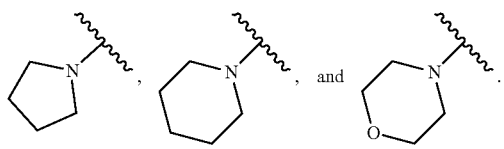 [SMILES: *N1CCCC1 ; *N1CCCCC1 ; *N1CCOCC1]

Additional antimicrobial compounds are also disclosed previously in U.S. Pat. No. 8,039,450, and patent application publication US 2009/0291917, the contents of which are hereby incorporated by reference in their entireties.

In one aspect, the volatile antimicrobial compound of the invention has the structure of formula (A):

$$R^A\text{-}L^A\text{-}G\text{-}L^B\text{-}R^B \quad (A),$$

wherein
each of $R^A$ and $R^B$ is independently a radical comprising an oxaborole moiety;
each of $L^A$ and $L^B$ is independently —O— or

each of R and R' is independently hydrogen, unsubstituted or substituted $C_{1-18}$-alkyl, arylalkyl, aryl, or heterocyclic moiety; and
G is a substituted or unsubstituted $C_{1-18}$-alkylene, arylalkylene, arylene, or heterocyclic moiety; and pharmaceutically acceptable salts thereof.

In one embodiment, the volatile compound is an antimicrobial compound. In another embodiment, the volatile compound has use against pathogens affecting meats, plants, or plant parts. In another embodiment, the -$L^A$-G-$L^B$- portion of formula (A) is derived from a diol or diamine compound. In a further embodiment, the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof. In another embodiment, the diamine compound is 1,2-ethylene diamine; 1,3-propylene diamine; or combinations thereof. In another embodiment, $L^A$ and $L^B$ are identical. In another embodiment, $L^A$ and $L^B$ are different. In another embodiment, each of $L^A$ and $L^B$ is independently —O— or —NH—. In another embodiment, $L^A$ and $L^B$ are identical. In another embodiment, $L^A$ and $L^B$ are different.

In another embodiment, the -$L^A$-G-$L^B$- portion of formula (A) comprises asymmetrical functional groups (i.e., asymmetrical bridges). In a further embodiment, the -$L^A$-G-$L^B$- portion of formula (A) comprises one hydroxyl group and one amine group. In a further embodiment, the -$L^A$-G-$L^B$- portion of formula (A) comprises an amino alcohol. In another embodiment, G is a substituted or unsubstituted $C_{1-8}$-alkylene. In a further embodiment, G is a substituted or unsubstituted $C_{1-4}$-alkylene. In a further embodiment, G is selected from —$CH_2$—, —$CH_2$—$CH_2$—, and —$CH_2$—$CH_2$—$CH_2$—.

In another embodiment, each of $R^A$ and $R^B$ is independently derived from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, $R^A$ and $R^B$ are identical. In another embodiment, $R^A$ and $R^B$ are different.

In another embodiment, at least one of $R^A$ and $R^B$ is selected from formula (B), (C), or (D):

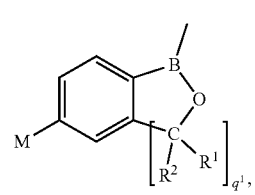
(B)

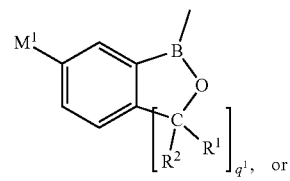
(C)

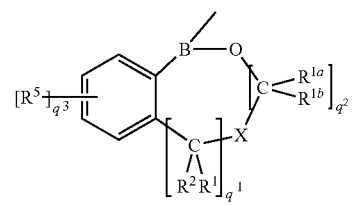
(D)

wherein q1 and q2 are independently 1, 2, or 3;
q3=0, 1, 2, 3, or 4;
B is boron;
M is hydrogen, halogen, —$OCH_3$, or —$CH_2$—O—$CH_2$—O—$CH_3$;
$M^1$ is halogen, —$CH_2OH$, or —$OCH_3$;
X is O, S, or $NR^{1c}$, wherein $R^{1c}$ is hydrogen, substituted alkyl, or unsubstituted alkyl;

$R^1$, $R^{1a}$, $R^{1b}$, $R^2$, and $R^5$ are independently hydrogen, OH, $NH_2$, SH, CN, $NO_2$, $SO_2$, $OSO_2OH$, $OSO_2NH_2$, substituted or unsubstituted cycloalkyl, substituted or unsubstituted heterocycloalkyl, substituted or unsubstituted aryl, or substituted or unsubstituted heteroaryl;

and pharmaceutically acceptable salts thereof.

Additional oxaborole moieties are also disclosed previously in U.S. Pat. No. 8,106,031, and International Patent Application WO 2007/131072A2, the contents of which are hereby incorporated by reference in their entireties.

In another embodiment, at least one of $R^A$ and $R^B$ has a structure of formula (F):

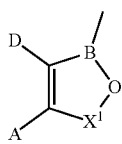

(F)

wherein A and D together with the carbon atoms to which they are attached form a 5, 6, or 7-membered fused ring which may be substituted by $C_{1-6}$-alkyl, $C_{1-6}$-alkoxy, hydroxy, halogen, nitro, nitrile, amino, amino substituted by one or more $C_{1-6}$-alkyl groups, carboxy, acyl, aryloxy, carbonamido, carbonamido substituted by $C_{1-6}$-alkyl, sulphonamido or trifluoromethyl or the fused ring may link two oxaborole rings; B is boron;

$X^1$ is a group —$CR^7R^8$ wherein $R^7$ and $R^8$ are each independently hydrogen, $C_{1-6}$-alkyl, nitrile, nitro, aryl, aralkyl or $R^7$ and $R^8$ together with the carbon atom to which they are attached form an alicyclic ring; and and pharmaceutically acceptable salts thereof.

Additional oxaborole moieties are also disclosed previously in U.S. Pat. No. 5,880,188, the content of which is hereby incorporated by reference in its entirety.

In another embodiment, at least one of $R^A$ and $R^B$ is selected from formula (E) or (G):

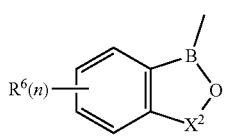

(E)

wherein each $R^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;
B is boron;
$X^2$=$(CR^{62})_m$ where m=1, 2, 3, or 4; or

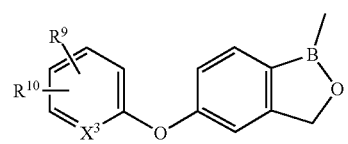

(G)

wherein $R^9$ is CN, $C(O)NR^{11}R^{12}$, or $C(O)OR^3$ wherein $R^3$ is hydrogen, substituted alkyl, or unsubstituted alkyl, $X^3$ is N, CH and $CR^{10}$;

$R^{10}$ is halogen, substituted or unsubstituted alkyl, $C(O)R^{14}$, $C(O)OR^{14}$, $OR^{14}$, $NR^{14}R^{15}$, wherein each of $R^{11}$, $R^{12}$, $R^{14}$, and $R^{15}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

and pharmaceutically acceptable salts thereof.

In a further embodiment when at least one of $R^A$ and $R^B$ has a structure of formula (G), $R^9$ is CN and $R^{10}$ is $R^b$.

In another embodiment, at least one of $R^A$ and $R^B$ has a structure selected from:

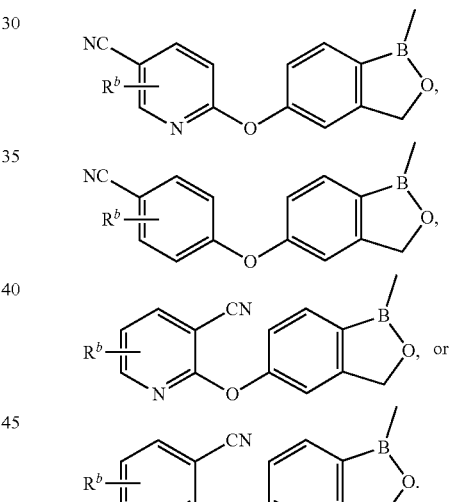

In another embodiment, at least one of $R^A$ and $R^B$ has a structure selected from:

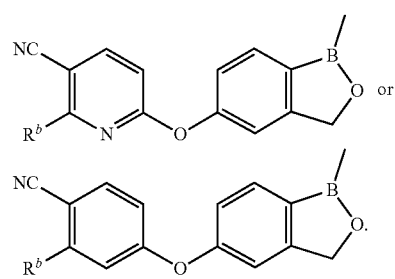

In another embodiment, at least one of $R^A$ and $R^B$ has a structure selected from:

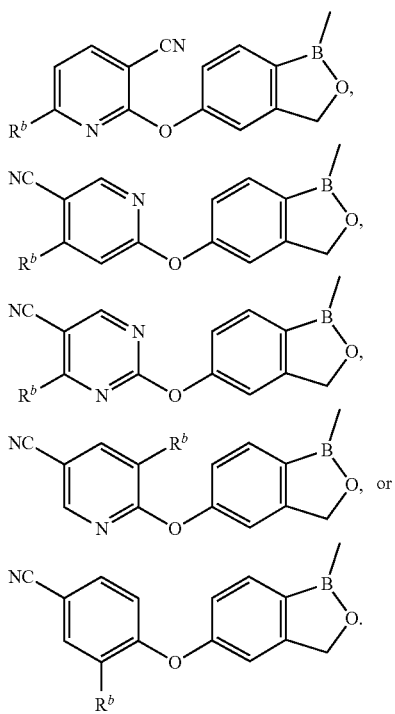

In another embodiment when at least one of $R^A$ and $R^B$ has a structure of formula (G), $R^9$ is —COOR$^3$ and $R^{10}$ is $R^b$.

In another embodiment, at least one of $R^A$ and $R^B$ has a structure selected from:

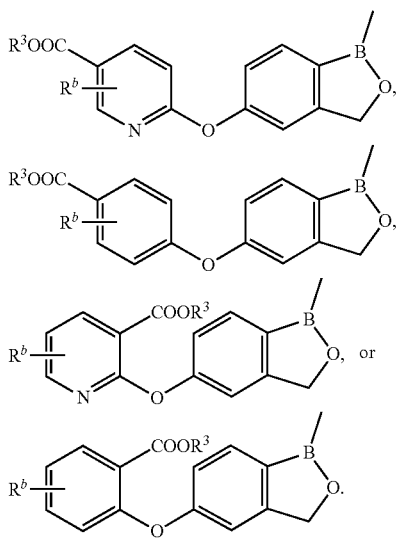

In another embodiment, at least one of $R^A$ and $R^B$ has a structure selected from:

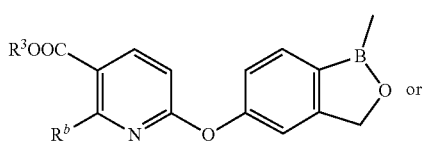

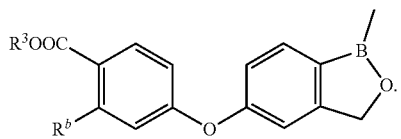

In another embodiment, at least one of $R^A$ and $R^B$ has a structure selected from:

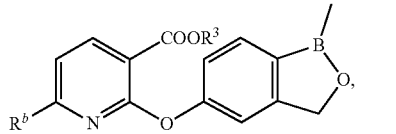

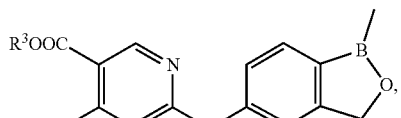

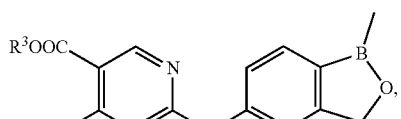

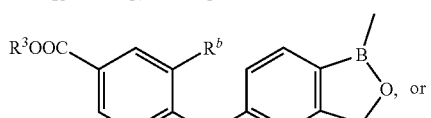

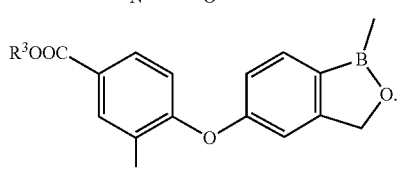

In another embodiment when at least one of $R^A$ and $R^B$ has a structure of formula (G), $R^9$ is —CONR$^1$R$^2$ and $R^{10}$ is $R^b$.

In another embodiment, each of $R^A$ and $R^B$ is independently selected from formula (B), (C), (D), (E), (F), or (G).

In another embodiment, the volatile compound of the invention is selected from:

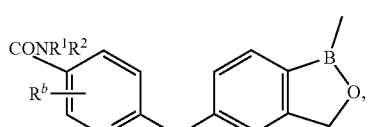

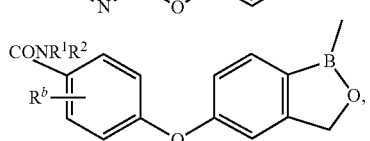

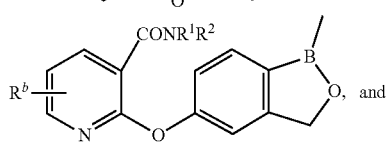

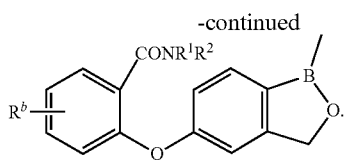

In another embodiment, the volatile compound of the invention is selected from:

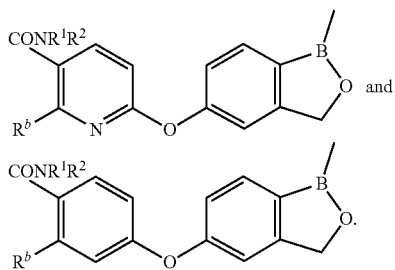

In another embodiment, the volatile compound of the invention is selected from:

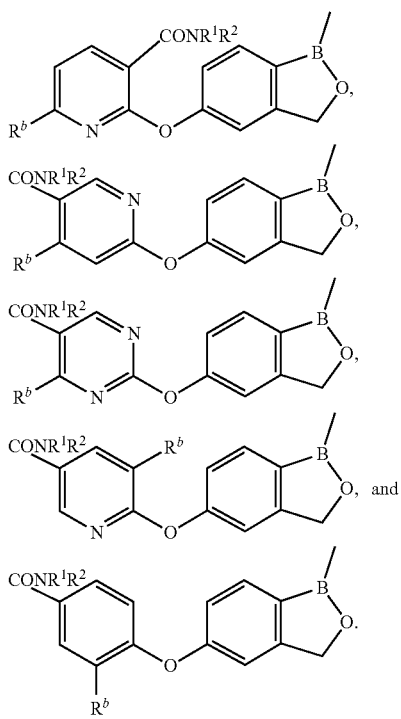

In one embodiment, $R^b$ is selected from fluorine and chlorine. In another embodiment, $R^b$ is selected from $OR^{20}$ and $NR^{21}R^{22}$. In another embodiment when $R^b$ is $OR^{20}$, $R^{20}$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $OR^{20}$, $R^{20}$ is selected from H, substituted or unsubstituted alkyl, substituted or unsubstituted heteroalkyl and substituted or unsubstituted cycloalkyl. In another embodiment when $R^b$ is $OR^{20}$, $R^{20}$ is unsubstituted $C_{1-6}$ alkyl. In another embodiment when $R^b$ is $OR^{20}$, $R^{20}$ is unsubstituted cycloalkyl. In another embodiment when $R^b$ is $OR^{20}$, $R^{20}$ is alkyl, substituted with a member selected from substituted or unsubstituted $C_{1-6}$ alkoxy. In another embodiment when $R^b$ is $OR^{20}$, $R^{20}$ is alkyl, substituted with at least one halogen. In another embodiment when $R^b$ $OR^{20}$, $R^{20}$ is alkyl, substituted with at least one oxo moiety.

In another embodiment when $R^b$ is $OR^{20}$, $R^{20}$ is a member selected from —$CH_3$, —$CH_2CH_3$, —$(CH_2)_2CH_3$, —$CH(CH_3)_2$, —$CH_2CF_3$, —$CH_2CHF_2$, —$CH_2CH_2(OH)$, —$CH_2CH_2(OCH_3)$, —$CH_2CH_2(OC(CH_3)_2)$, —$C(O)CH_3$, —$CH_2CH_2OC(O)CH_3$, —$CH_2C(O)OCH_2CH_3$, —$CH_2C(O)OC(CH_3)_3$, —$(CH_2)_3C(O)CH_3$, —$CH_2C(O)OC(CH_3)_3$, cyclopentyl, cyclohexyl,

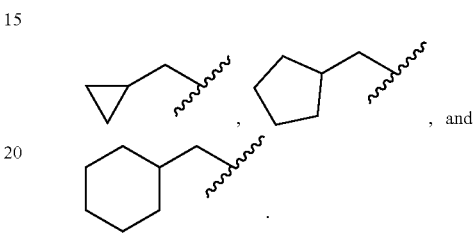

In another embodiment when $R^b$ is $NR^{21}R^{22}$, $R^{21}$ and $R^{22}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $NR^{21}R^{22}$, $R^{21}$ is H or unsubstituted alkyl; and $R^{22}$ is unsubstituted alkyl or alkyl substituted with a member selected from hydroxyl, phenyl, unsubstituted alkoxy and alkoxy substituted with a phenyl. In a further embodiment when $R^b$ is $NR^{21}R^{22}$, $R^{21}$ is H or $CH_3$.

In another embodiment when $R^b$ is $NR^{21}R^{22}$, $R^{21}$ and $R^{22}$ are independently selected from substituted or unsubstituted alkyl. In another embodiment when $R^b$ is $NR^{21}R^{22}$, $R^{21}$ is unsubstituted alkyl; and $R^{22}$ is substituted or unsubstituted alkyl. In another embodiment when $R^b$ is $NR^{21}R^{22}$, $R^{21}$ is unsubstituted alkyl; and $R^{22}$ is alkyl, substituted with a member selected from substituted or unsubstituted alkoxy and hydroxyl. In another embodiment when $R^b$ is $NR^{21}R^{22}$, $R^{21}$ is unsubstituted alkyl; and $R^{22}$ is alkyl, substituted with unsubstituted alkoxy. In another embodiment when $R^b$ is $NR^{21}R^{22}$, $R^{21}$ is unsubstituted alkyl; and $R^{22}$ is alkyl, substituted with alkoxy, substituted with phenyl. In another embodiment when $R^b$ is $NR^{21}R^{22}$, $R^{21}$ is unsubstituted alkyl; and $R^{22}$ is alkyl, substituted with unsubstituted alkoxy. In another embodiment when $R^b$ is $NR^{21}R^{22}$, $R^{21}$ and $R^{22}$ together with the nitrogen to which they are attached, are combined to form a 4- to 8-membered substituted or unsubstituted heterocycloalkyl ring. In another embodiment when $R^b$ is $NR^{21}R^{22}$, $R^{21}$ and $R^{22}$ together with the nitrogen to which they are attached, are combined to form a 5- or 6-membered substituted or unsubstituted heterocycloalkyl ring.

In another embodiment, $R^b$ is selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph))$, $NH(CH_2Ph)$, $NH(C(CH_3)_3)$ and $NH(CH_2CH_2OH)$. In another embodiment, $R^b$ is selected from

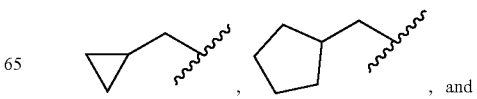

-continued

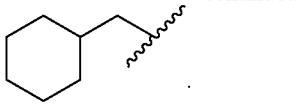

Additional oxaborole moieties are also disclosed previously in U.S. Pat. No. 8,039,450, and patent application publication US 2009/0291917, the contents of which are hereby incorporated by reference in their entireties.

In another embodiment, the compound provided has a structure of formula (A1) or (A2):

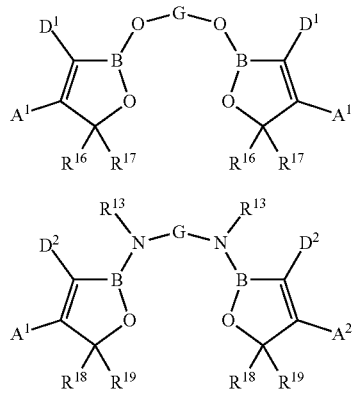

wherein each of $A^1$, $A^2$, $D^1$, and $D^2$ is independently hydrogen, substituted or unsubstituted $C_1$-$1_8$-alkyl, arylalkyl, aryl, or heterocyclic; or $A^1$ and $D^1$, or $A^2$ and $D^2$ together form a 5, 6, or 7-membered fused ring which is substituted or unsubstituted;

each of $R^{13}$, $R^{16}$, $R^{17}$, $R^{18}$, and $R^{19}$ is independently hydrogen, substituted or unsubstituted $C_{1-6}$-alkyl, nitrile, nitro, aryl or aryl alkyl; or $R^{16}$ and $R^{17}$, or $R^{18}$ and $R^{19}$ together form an alicyclic ring which is substituted or unsubstituted;

B is boron; and

G is a substituted or unsubstituted $C_{1-18}$-alkylene, arylalkylene, arylene, or heterocyclic moiety.

In another embodiment, each of $R^A$ and $R^B$ is independently

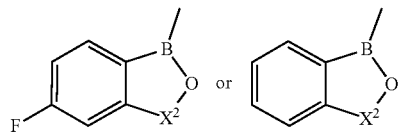

wherein $X^2=(CR^6_2)_m$ and m=1, 2, 3, or 4.

In another embodiment, each of $R^A$ and $R^B$ is independently

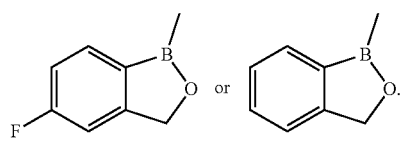

In another embodiment, the compound provided has the structure of

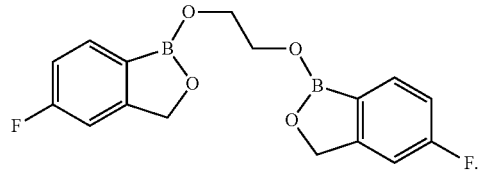 [SMILES: Fc1ccc2c(c1)COB2OCCOB1OCc2cc(F)ccc21]

Additional oxaborole moieties are also disclosed previously in U.S. Pat. No. 5,880,188, the content of which is hereby incorporated by reference in its entirety.

Also provided are methods for treating human infections, methods for using a volatile antimicrobial compound against human pathogens, and/or methods for treating human diseases.

In one embodiment, the method provided comprises
 (a) providing a volatile compound as provided herein in gaseous form; and
 (b) contacting or treating affected areas with an effective amount of the volatile compound as provided herein in gaseous form.

In another embodiment, the method provided comprises
 (a) placing affected areas in a container, confined or closed environment; and
 (b) introducing into the container, confined or closed environment and in contact with the affected areas an effective amount of the volatile compound as provided herein in gaseous form.

In another embodiment, the method provided comprises contacting or treating the affected areas with an atmosphere comprising an effective amount of the volatile compound as provided herein in gaseous form.

In one embodiment, the contacting comprises applying the volatile antimicrobial compound to the surface of a material or absorbing or imbedding it into a material by ways selected from the group consisting of spray, mist, drench, or direct gaseous treatment, and combinations thereof. In a further embodiment, the gas treatment is released from the group consisting of release from a sachet, release from a synthetic or natural film, fibrous material, and/or release from a liner or powder and combinations thereof.

Description of common human infections. Vaginal yeast infections—most women have had a vaginal yeast infection at some point in their lifetime. Fungi are often found in small amounts in the human vagina, mouth, digestive tract, and on the skin. Usually fungus at reasonable levels does not cause disease or symptoms. Candida and the many other germs, including fungi that normally live in the vagina keep each other in balance. However, sometimes the number of Candida species increases, leading to a yeast infection.

Exemplary pathogens leading to yeast infections and encompassed by the present invention comprise Candida spp. including C. albicans, C. tropicalis, C. glabrata, C. krusei, C. parapsilosis, C. dubliniensis, and C. lusitaniae. An illustrative example of a fungal pathogen causing human yeast infections, including vaginal yeast infections, is Candida albicans. Candida albicans is a common type of fungus, as well as a causal agent that is responsible for 50-90% of cases of vaginal candidiasis in humans.

An additional exemplary fungal pathogen of the present application is Candida krusei. Candida krusei, also called

*Issatchenkia orientalis* (*I. orientalis*), is another *Candida* fungal species that has been found to cause 0-9% of cases of vaginal candidiasis.

Vaginosis can be treated with antibiotics metronidazole (for example Flagyl and MetroGel), clindamycin (for example Cleocin and Clindesse), and tinidazile (for example Tindamax), which can be taken orally (by mouth) or vaginally. Combinations of these agents and the volatile compounds disclosed herein (for example benzoxaborole) are also provided.

Athlete's foot (otherwise known as ringworm of the foot, tinea pedis, tinea pedum, or moccasin foot) is a common and contagious dermatophytic fungal infection of the skin that causes scaling, flaking, and itching of the affected areas. Symptoms are caused by fungi for example *Epidermophyton floccosum*, or fungi of the *Trichophyton* genus including *T. rubrum* or *T. mentagrophytes*. The disease is typically transmitted in moist communal areas where people walk barefoot, such as showers or bathhouses, and requires a warm moist environment, (e.g., the inside of a shoe) to incubate. The condition typically affects the feet, but may infect or spread to other areas of the body such as the groin and tends to spread to areas of skin that are kept hot and moist, for example with insulation, body heat, and sweat. The fungal agents responsible for infection may be picked up by walking barefoot in an infected area or using an infected towel. Infection can be prevented by limiting the use of occlusive footwear and remaining barefoot. Tinea is the name of a group of diseases caused by a fungus. Types of tinea include ringworm, athlete's foot and jock itch. These infections are usually not serious, but they can be uncomfortable. Affected areas may include skin (red skin rash that forms a ring around normal-looking skin); head (scalp ringworm causes itchy, red patches on your head—it can leave bald spots); foot and/or toes (Athlete's foot may cause itching, burning and cracked skin between your toes); and groin (jock itch causes an itchy, burning rash in your groin area).

Most cases of athlete's foot can be cured with over-the-counter antifungal products and basic good hygiene. Products are applied as antifungal powder, antifungal creams, and sprays applied directly to the infected area. Continue treatment for one to two weeks after the infection has cleared to prevent it from recurring. Combinations of these commonly used agents and the volatile compounds disclosed herein (for example benzoxaborole) are also provided.

Those skilled in the art would understand certain variation can exist based on the disclosure provided. Thus, the following examples are given for the purpose of illustrating the invention and shall not be construed as being a limitation on the scope of the invention or claims.

EXAMPLES

Example 1

For testing activity against fungi pathogens, an in vitro inhibition assay for volatile antimicrobial compounds is developed using 12-Well (7 milliliter (mL) volume per well) microtiter plates. A 3-mL volume of full-strength Potato Dextrose Agar (PDA) is added to each well. After cooling, 1 microliter (μL) of 1×10$^6$ per mL *Botrytis cinerea* spore suspension is spot pipetted to the center of the agar. For the first experiment, inoculated plates are allowed to germinate for 5 days at 4° C. For the second experiment, plates are inoculated immediately prior to volatile fungicide treatment. Small Whatman #1 filter disks (Cat. No. 1001-0155) are placed, in duplicate, on the underside of a polyethylene PCR plate sealing film.

TABLE 1

| Results of *in vitro* assay for volatile fungicide | |
|---|---|
| Rate of Compound A (mg per disk) | *Botrytis* inhibition % (*in vitro*) |
| 1.25 | 100% |
| 0.63 | 100% |
| 0.31 | 100% |
| 0.16 | 100% |
| 0.08 | 100% |
| 0.04 | 100% |
| 0.023 | 100% |
| 0.01 | 100% |
| 0.005 | 100% |
| 0.0024 | 85% |
| 0.001 | 69% |
| 0.0006 | 46% |
| Control | 0% |

For determination of the minimum inhibitory concentration (MIC), Compound A (5-fluoro-1,3-dihydro-1-hydroxy-2,1-benzoxaborole) is diluted in acetone, and the appropriate amount of compound is added to disks in a dose dependent manner (1.25 to 0.0006 milligrams per disk (mg/disk)). The acetone is permitted to evaporate for 5 minutes. The headspace around the *Botrytis cinerea* inoculum is then sealed inside the well by the film with the adhering disk containing the fungicide. Plates are inverted, placed over the treated disks and sealed to prevent any of the chemical from flaking from the disk and falling onto the inoculated agar. After 14 days of storage at 4° C., cultures are evaluated for percent growth relative to control. Regardless of whether the spores had germinated for 5 days, or if the treatment commenced soon after inoculation of the plates (~15 minutes); there is 100% control of the fungal pathogen down to 0.005 mg.

Experimental results are summarized in Table 1. The results suggest that Compound A is able to kill *Botrytis cinerea* spores and inhibit mycelial growth at the same concentration. Thus, Compound A shows 100% efficacy in the in vitro inhibition of fungal growth at a rate of 0.005 mg/disk.

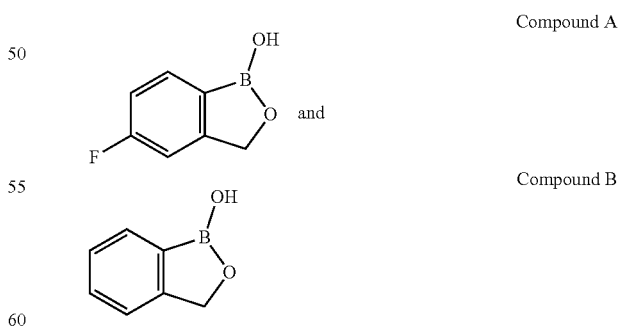

Compound A

Compound B

Compound B (2-(hydroxymethyl)phenylboronic acid cyclic monoester, a des-fluoro analogue of Compound A), is evaluated in a similar manner. The compound is applied to the Whatman filter paper at rates from 0.5 mg to 0.0039 mg/disk. Results show that Compound B inhibits 100% *Botrytis cinerea* at a rate of 0.0078 mg/disk.

Example 2

For testing activity against bacteria pathogens, 12-Well (7 mL volume per well) microtiter plates are used for the in vitro inhibition assay for volatile antimicrobial compounds. A 3-mL volume of full-strength $L^B$ Agar is added to each well. After cooling, 15 µL of *Escherichia coli*, adjusted to an optical density of 0.02 to 0.035, and further diluted 1/10 is pipetted to the center of the agar and tilted to distribute uniformly. Small Whatman #1 filter disks (Cat. No. 1001-0155) are placed, in duplicate, on the underside of a polyethylene polymerase chain reaction (PCR) plate sealing film. For determination of the minimum inhibitory concentration (MIC), Compound A is diluted in acetone, and 5 mg of compound is added to the disks. The acetone is permitted to evaporate for 5 minutes. The headspace around the *Escherichia coli* inoculum is then sealed inside the well by the film with the adhering disk containing the fungicide. Plates are inverted, placed over the treated disks and sealed to prevent any of the chemical from flaking from the disk and falling onto the inoculated agar. After 3 days of storage at 4° C., cultures are transferred to 23° C. for an additional 2 days, and then evaluated for colony growth relative to control. Experimental results are summarized in Table 2. The results suggest that Compound A is able to inhibit *Escherichia coli*.

TABLE 2

Results of *in vitro* assay for volatile fungicide

| Rate of Compound A (mg per disk) | Colony Rating |
|---|---|
| 5.00 | 1 |
| Untreated | 3 |
| Not Inoculated | 0 |

Colony Rating:
0 = No colonies
1 = Micro colonies not connected
2 = Small colonies with some merging
3 = Large colonies merging together

Example 3

For testing activities against additional fungi pathogens, 12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of $1 \times 10^5$ per mL *Botrytis cinerea, Penicillium expansum, Alternaria alternata, Monilinia fructicola* or *Glomerella cingulata* spore suspension is spot-pipetted to the center of the agar. Plates are inoculated immediately prior to volatile fungicide treatment. A Whatman #1 filter disk (Cat. No. 1001-0155) is placed, in duplicate, on the underside of a polyethylene PCR plate sealing film. For determination of the minimum inhibitory concentration (MIC), compounds are diluted in acetone, and the appropriate amount of compound is added to the disks in a dose dependent manner to achieve a final headspace concentration of 1142.9 to 0.6 mg/L. The acetone is permitted to evaporate for 5 minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., the cultures are evaluated for percent growth relative to control based on measurement of fungal colony diameter. Experimental results are summarized in Table 3. The results indicate that benzoxaborole compounds have excellent in vitro activity against five selected fungal pathogens.

TABLE 3

MIC (mg/L, headspace concentration) of numerous benzoxaborole compounds applied as a volatile treatment against numerous fungal pathogens (Compound 10 is the same as Compound A, and Compound 11 is the same as Compound B).

| Structure | Cmpd # | MIC (mg/L) | | | | |
|---|---|---|---|---|---|---|
| | | BOTRCI | PENIEX | ALTEAL | MONIFC | GLOMCI |
| benzoxaborole-O-CH₃ | 6 | 2.2 | 17.9 | 4.5 | 8.9 | 17.9 |
| benzoxaborole-O-(CH₂)₃-O-CH₃ | 7 | 2.2 | 17.9 | 8.9 | 8.9 | 71.4 |
| benzoxaborole-O-(CH₂)₂-O-CH₃ | 8 | 2.2 | 35.7 | 8.9 | 4.5 | 71.4 |

TABLE 3-continued

MIC (mg/L, headspace concentration) of numerous benzoxaborole compounds
applied as a volatile treatment against numerous fungal pathogens (Compound 10 is
the same as Compound A, and Compound 11 is the same as Compound B).

| Structure | Cmpd # | MIC (mg/L) | | | | |
| --- | --- | --- | --- | --- | --- | --- |
| | | BOTRCI | PENIEX | ALTEAL | MONIFC | GLOMCI |
| (structure) | 9 | 2.2 | 8.9 | 8.9 | 8.9 | 35.7 |
| (structure) | 10 | 2.2 | 2.2 | <0.6 | <0.6 | <0.6 |
| (structure) | 11 | 4.5 | 17.9 | 4.5 | 2.2 | 35.7 |
| (structure) | 30 | 2.2 | 8.9 | 2.2 | 2.2 | n/a |
| (structure) | 34 | <0.6 | 2.2 | 2.2 | n/a | n/a |
| (structure) | 200 | 10.6 | 68.3 | 7.3 | 6.3 | n/a |
| (structure) | 201 | 3.8 | 29.5 | 16.1 | 8.5 | 9.3 |

BOTRCI = *Botrytis cinerea*
PENIEX = *Penicillium expansum*
ALTEAL = *Alternaria alternata*
MONIFC = *Monilinia fructicola*
GLOMCI = *Glomerella cingulata*

Example 4

12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of 1×10$^5$ per mL *Botrytis cinerea* and *Penicillium expansum* spore suspension is spot-pipetted to the center of the agar. Plates are inoculated immediately prior to volatile fungicide treatment. A Whatman #1 filter disk (Cat. No. 1001-0155) is placed, in duplicate, on the underside of a polyethylene PCR plate sealing film. For determination of the minimum inhibitory concentration (MIC), compounds are diluted in acetone, and the appropriate amount of compound is added to the disks in a dose dependent manner to achieve a final headspace concentration of 35.7 to 0.03 mg/L. The acetone is permitted to evaporate for 5 minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., the cultures are evaluated for percent growth relative to control based on measurement of fungal colony diameter. Experimental results are summarized in Table 4. The results indicate that numerous benzoxaborole compounds have excellent in vitro activity against two selected fungal pathogens.

TABLE 4

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | MIC (mg/L) PENIEX |
|---|---|---|---|
| 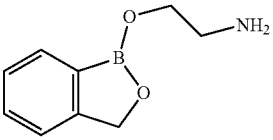 [SMILES: NCCOB1OCc2ccccc21] | 21 | 1.1 | 35.7 |
| 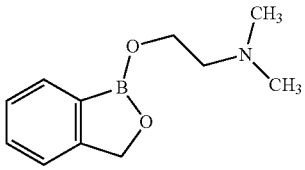 | 22 | 4.5 | 35.7 |
| 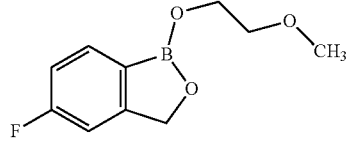 | 38 | 0.6 | 8.9 |
| 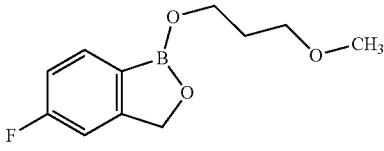 [SMILES: COCCCOB1OCc2cc(F)ccc21] | 39 | 0.6 | 8.9 |
| 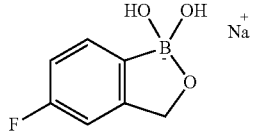 | 54 | 0.6 | 4.5 |
| 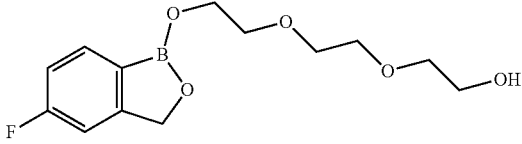 [SMILES: OCCOCCOCCOB1OCc2cc(F)ccc21] | 55 | 4.5 | >35.7 |
| 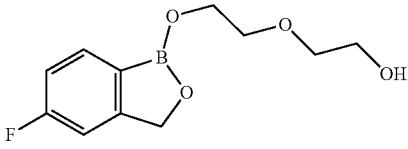 [SMILES: OCCOCCOB1OCc2cc(F)ccc21] | 62 | 2.2 | 8.9 |
| 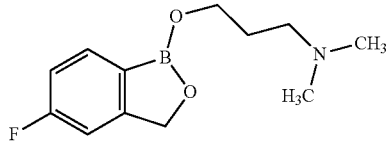 [SMILES: CN(C)CCCOB1OCc2cc(F)ccc21] | 63 | 1.1 | 17.9 |

TABLE 4-continued

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | MIC (mg/L) PENIEX |
|---|---|---|---|
| 5-F benzoxaborole-O-(CH2)3-NH2 | 64 | 1.1 | 8.9 |
| 5-F benzoxaborole-O-CH2CH2-N(CH3)-CH2CH2OH | 72 | 35.7 | >35.7 |
| 5-F benzoxaborole-O-CH2CH2-NH-CH2CH2OH | 73 | 35.7 | >35.7 |
| 5-F benzoxaborole-O-CH2CH2-N(CH3)2 | 74 | 2.2 | 35.7 |
| 5-F benzoxaborole-O-(CH2)6-OH | 86 | 0.6 | 8.9 |
| 5-F benzoxaborole-O-CH2CH2-NH-CH3 | 87 | 0.6 | 8.9 |
| 5-F benzoxaborole-OH · N(CH3)2H | 105 | 0.6 | 4.5 |
| benzoxaborole-OH, 3-morpholino | 114 | 17.9 | >35.7 |

TABLE 4-continued
MIC (mg/L) of numerous benzoxaborole compounds applied as a volatile treatment against *Botrytis cinerea* and *Penicillium expansum* fungal pathogens.
| Structure | Cmpd # | MIC (mg/L) BOTRCI | MIC (mg/L) PENIEX |
|---|---|---|---|
| 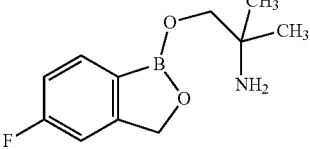 | 115 | 0.6 | 8.9 |
| 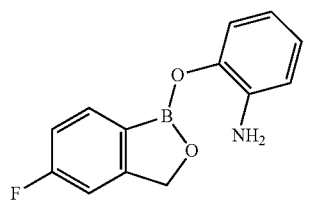 [SMILES: Nc1ccccc1OB1OCc2cc(F)ccc21] | 116 | 1.1 | 8.9 |
| 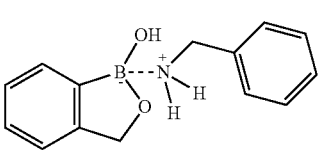 | 121 | 4.5 | 17.9 |
| 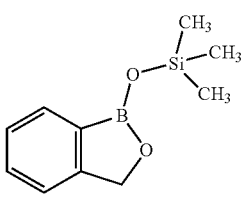 | 122 | 2.2 | 17.9 |
| 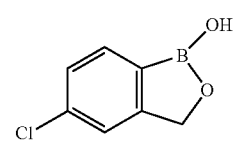 [SMILES: OB1OCc2cc(Cl)ccc21] | 124 | 4.5 | 8.9 |
| 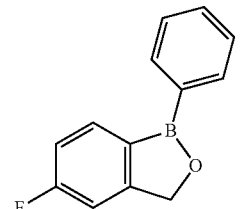 | 127 | 2.2 | 4.5 |
| 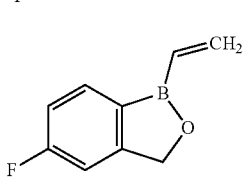 | 129 | 4.5 | 8.9 |
| 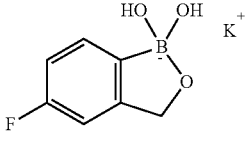 | 130 | 1.1 | 4.5 |

TABLE 4-continued

MIC (mg/L) of numerous benzoxaborole compounds applied as a
volatile treatment against *Botrytis cinerea* and *Penicillium expansum*
fungal pathogens.

| Structure | Cmpd # | MIC (mg/L) BOTRCI | PENIEX |
|---|---|---|---|
| (structure) | 132 | 1.1 | 4.5 |
| (structure) | 133 | 8.9 | 35.7 |
| (structure) | 134 | 17.9 | >35.7 |
| (structure) | 135 | 17.9 | >35.7 |
| (structure) | 136 | 8.9 | >35.7 |
| (structure) | 137 | 0.3 | 1.1 |

TABLE 4-continued

MIC (mg/L) of numerous benzoxaborole compounds applied as a volatile treatment against *Botrytis cinerea* and *Penicillium expansum* fungal pathogens.

| Structure | Cmpd # | MIC (mg/L) BOTRCI | PENIEX |
|---|---|---|---|
| (benzoxaborole with F at position, OH) | 202 | 35.7 | 142.9 |
| (benzoxaborole with F, OH) | 203 | 8.9 | 142.9 |
| (benzoxaborole with two F, OH) | 204 | 8.9 | >35.7 |

BOTRCI = *Botrytis cinerea* (gray mold)
PENIEX = *Penicillium expansum* (blue mold)

Example 5

12-Well (6.5 mL volume per well) microtiter plates are used for the in vitro inhibition assay for volatile antimicrobial compounds A and B against additional fungal pathogens.

A 3-mL volume of full-strength Potato Dextrose Agar (PDA) is added to each well. After cooling, 1 L of $1\times10^5$ spores per mL of *Botrytis cinerea, Penicillium expansum, Alternaria alternata, Glomerella cingulata, Penicillium digitatum, Monilinia fruticola, Aspergillus brasiliensis, Colletotrichum acutatum, Fusarium sambucinum, Phytophthora capsici, Geotrichum candidum, Aspergillus niger, Diplodia gossypina* or *Diaporthe citrii* suspension is spotted onto the center of the agar. A Whatman #1 filter disk (Cat. No. 1001-0155) is placed, in duplicate, on the underside of a polyethylene PCR plate sealing film. For determination of the minimum inhibitory concentration (MIC), test compounds are diluted in acetone, and the appropriate amount of compound is added to the disks in a dose dependent manner to achieve a final headspace concentration of 35.7 to 0.03 mg/L. The acetone is permitted to evaporate for five minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., cultures are evaluated for percent growth relative to control. Results shown in Table 5 demonstrate the ability of benzoxaborole compounds A and B to control the growth of numerous fungal pathogens through volatile activity.

TABLE 5

MIC (mg/L) of Compounds A and B applied as a volatile against numerous fungal pathogens

| Pathogens | Compound A MIC | Compound B MIC |
|---|---|---|
| B. cinerea | 2.2 | 4.5 |
| P. expansum | 1.1 | 8.9 |
| M. fruticola | 2.2 | 1.1 |
| A. alternata | 2.2 | 2.2 |
| G. cingulata | 17.9 | 35.7 |
| P. digitatum | 2.2 | 4.5 |
| A. brasiliensis | 2.2 | 0.6 |
| C. acutatum | 4.4 | 8.9 |
| F. sambucinum | 1.1 | 4.5 |
| P. capsici | 1.1 | n/a |
| G. candidum | 8.9 | 8.9 |
| A. niger | 2.2 | 1.1 |
| M piriformis | 1.1 | 2.2 |
| D. gossypina | 1.1 | 4.5 |
| D. citrii | 2.2 | 17.9 |

Example 6

12-Well (6.5 mL volume per well) microtiter plates are used for the in vitro inhibition assay for volatile antimicrobial Compound A against additional bacterial pathogens. A 3-mL volume of Nutrient agar is added to each well and allowed to dry before introducing the pathogen. *Escherichia coli, Pectobacterium carotovorum, Xanthomonas axonopodis* and *Salmonella enterica* cell suspensions are adjusted to an optical density of 0.2 to 0.35, and further diluted 1/10, and 15 µL is pipetted to the center of each well and tilted to distribute uniformly. A Whatman #1 filter paper (CAT 1001-0155) is placed on the underside of a polyethylene PCR plate sealing film. For determination of minimum bactericidal concentration (MBC), Compound A is diluted in acetone, and 50 µL are applied to the disks, in duplicate, in a dose dependent manner in order to achieve a final headspace concentration of 71.4 to 0.03 mg/L. The acetone is permitted to evaporate for 5 minutes. The films with the treated disks are then applied over the inoculated plates and sealed. Plates are inverted, and incubated at 23° C. for 48 hours. After the incubation period, the bacteria colonies are dislodged in sterile water containing tween 80 (0.001%) and the optical density (OD; 600 nm) is determined. Results are summarized in Table 6, where the headspace concentration required to control at least 80% of bacterial growth is reported. Compound A shows good antimicrobial activity against numerous bacteria in this in vitro assay.

TABLE 6

| Rate (mg/L) of Compound A offering at least 80% control against bacterial pathogens | | | |
|---|---|---|---|
| E. coli | P. carotovorum | X. axonopodis | S. enterica |
| 35.7 | 2.2 | 4.5 | 17.9 |

Example 7

An in vitro assay is used to evaluate the ability of Compound A to volatilize from different materials and control fungal growth. PTFE-Coated Fiberglass (8577K81), Fiberglass (8816K1), Silica (8799K3), Aramid and Fiberglass blend (8821K4), Vinyl-Coated Polyester (8843K31), Acrylic-Coated Fiberglass (8838K2), Silicone-Coated Fiberglass (87815K1), Aramid (1206T1) (all McMaster-Carr, Santa Fe Springs, Calif.), Polyethylene PCR sealing film, Cellulose (Whatman #1, Cat no. 1001-0155), PTFE (Cole Parmer, Cat no. 36229-32), and Category-1 cardboard were cut into disks of 15 mm diameter. 12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of $1 \times 10^5$ per mL Botrytis cinerea spore suspension is spot-pipetted to the centre of the agar. Plates are inoculated immediately prior to volatile fungicide treatment.

TABLE 7

Effects of different materials on the volatile release of Compound A and the subsequent in vitro inhibition (MIC) of Botrytis cinerea.

| Material | MIC (mg/L) |
|---|---|
| Polyethylene PCR Film | 0.28 |
| PTFE- Coated Fiberglass | 0.56 |
| Fiberglass | 0.56 |
| Cellulose | 0.56 |
| Silica | 0.56 |
| Aramid and Fiberglass | 0.56 |
| Vinyl-Coated Polyester | 0.56 |

TABLE 7-continued

Effects of different materials on the volatile release of Compound A and the subsequent in vitro inhibition (MIC) of Botrytis cinerea.

| Material | MIC (mg/L) |
|---|---|
| Acrylic-Coated Fiberglass | 0.56 |
| Silicone- Coated Fiberglass | 0.56 |
| PTFE | 1.1 |
| Cardboard | 2.2 |
| Aramid | 2.2 |

The various materials are placed, in duplicate, on the underside of a polyethylene PCR plate sealing film. For determination of the minimum inhibitory concentration (MIC), compounds are diluted in acetone, and the appropriate amount of compound is added to the materials in a dose dependent manner to achieve a final headspace concentration of 35.7 to 0.03 mg/L. The acetone is permitted to evaporate for five minutes. The headspace around the Botrytis cinerea inoculum is then sealed inside the well by the film with the adhering disk of material containing the fungicide. Plates are inverted, placed over the treated disks and sealed to prevent any of the chemical from flaking from the disk and falling onto the inoculated agar. After three days of storage at 23° C., the cultures are evaluated for percent growth relative to control based on measurement of fungal colony diameter. Experimental results are summarized in Table 7. The results indicate that Compound A can volatilize from numerous materials to inhibit the in vitro growth of Botrytis cinerea with similar levels of control.

Example 8

An in vitro assay is used to evaluate the ability of compound A to volatilize from different materials and control fungal growth. Cardboard box (Category 1), PET plastic (Polyethylene terepthalate—PET) and Polyethylene are used. The materials are cut into equal dimensions (10×19 cm²) and placed inside a 36-L acrylic desiccator cabinet (Fisher Scientific, cat no. 08-642-23C) in duplicate.

TABLE 8

Effects of different materials on the volatile release of Compound A and the subsequent in vitro inhibition of Botrytis cinerea

| Material | Incidence (%) | | |
|---|---|---|---|
| | Clamshell | Cardboard | Polyethylene |
| Rate (mg/L) | | | |
| 0.3 | 4.1 | 9.3 | 4.9 |
| 0.06 | 100.0 | 91.7 | 86.7 |
| 0.012 | 100.0 | 100.0 | 99.0 |

Compound A is dissolved in acetone and 100 µL of the solution pipetted into a glass tube. The acetone is allowed to evaporate for 1 minute at 60° C. Compound A is then introduced as a gas into the cabinets by a sublimation device (copper tube heated to 180° C. with fan flow at 0.5 L/min) to achieve a final headspace concentration of 0.3, 0.06 and 0.012 mg/L). The chambers are then incubated at 23° C. for 24 hours, then treated materials are carefully removed and placed inside a clean 10.8 cup SnapWare airtight container (Model #109842) containing a 10-cm diameter Petri dish with PDA and inoculated with 1 μL of 1×10 spores/mL of *B. cinerea*. The containers are then tightly sealed for 3 days at 23° C. After 3 days of storage, cultures are evaluated for percent growth relative to control. Table 8 demonstrates the ability of benzoxaborole compounds A to control the growth of *B. cinerea* through volatile activity.

Example 9—Preparation of Sample 1

3.20 g of 5-fluoro-1,3-dihydro-1-hydroxy-2,1-benzoxaborole (21.2 mmol) and 3.20 g of ethylene glycol (51.6 mmol) are heated in 40 g of toluene. The toluene water azeotrope is distilled out of the system until the head temperature reached 110° C. The toluene is removed via rotary evaporator and the excess ethylene glycol is removed by kugelrohr distillation at about 20 torr and 100° C. bath temperature. Recrystallization from toluene generates 2.95 g of white crystals, mp 145-149° C. Proton nmr shows spectra and integration consistent with the two to one product below:

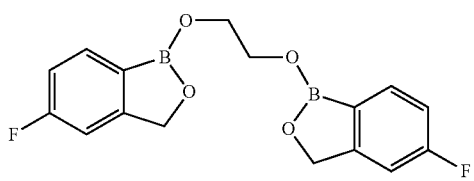 [SMILES: Fc1ccc2c(c1)COB2OCCOB1OCc2cc(F)ccc21]

Example 10—Preparation of Sample 2

3.00 g of 1,3-dihydro-1-hydroxy-2,1-benzoxaborole (22.4 mmol) and 3.00 g of ethylene glycol (46.9 mmol) are heated in 40 g of toluene. The toluene water azeotrope is distilled out of the system until the head temperature reached 110° C. The toluene is removed via rotary evaporator and the excess ethylene glycol is removed by kugelrohr distillation at about 20 torr and 100° C. bath temperature. Recrystallization from toluene generates 2.49 g of white crystals, mp 118-120.5° C. Proton NMR shows spectra and integration consistent with the two to one product.

Example 11—Preparation of Sample 3

3.17 g of 5-fluoro-1,3-dihydro-1-hydroxy-2,1-benzoxaborole (21.0 mmol) and 3.22 g of pinacol (27.3 mmol) are heated in 40 g of toluene. The toluene water azeotrope is distilled out of the system until the head temperature reached 110° C. The toluene is removed via rotary evaporator and the excess pinacol is removed by kugelrohr distillation at about 20 torr and 120° C. bath temperature. Recrystallization from hexane generates 3.21 g of white crystals, mp 81-89° C. Proton NMR shows spectra and integration consistent with the two to one product.

Example 12—Preparation of Sample 4

3.0 g of 5-fluoro-1,3-dihydro-1-hydroxy-2,1-benzoxaborole (19.9 mmol) and 2.5 g of 1,2-propanediol (propylene glycol; 32.9 mmol) are heated in 40 g of toluene. The toluene water azeotrope is distilled out of the system until the head temperature reached 110° C. The toluene is removed via rotary evaporator and the excess propylene glycol is removed by kugelrohr distillation at about 20 torr and 110° C. bath temperature. Recrystallization from hexane generates 3.49 g of white crystals, mp 65.5-68.5° C. Proton NMR shows spectra and integration consistent with the two to one product.

Example 13—In Vitro Analysis 12-well (6.5 ml volume per well) microtiter plates are used for the in vitro inhibition assay for volatile antimicrobial compounds. A 3-ml volume of full-strength Potato Dextrose Agar (PDA) is added to each well. After cooling, 1 μL of 1×10$^1$ spores per ml *Botrytis cinerea* (ATCC #204446) spore suspension is spot pipetted to the agar in the centre of the well.

TABLE 9

Antimicrobial activities of Samples 1-4 (50 μl/disk)

| | MIC mg/l | | | | |
|---|---|---|---|---|---|
| ID | Botrytis cinerea | Penicillium expansum | Alternaria alternata | Monilinia fructicola | Glomerella cingulata |
| Sample 1 | <0.6 | 8.9 | 2.2 | — | — |
| Sample 2 | <0.6 | 8.9 | 8.9 | 35.7 | 142.9 |
| Sample 3 | <0.6 | 4.5 | 2.2 | — | — |
| Sample 4 | <0.6 | 8.9 | 1.1 | — | — |

Whatman #1 filter disks (1.5 cm; Cat. No. 1001-0155) are placed on the underside of a polyethylene PCR plate sealing film. For determination of the minimum inhibitory concentration (MIC), test compounds are diluted in acetone, in duplicate, and 50 μl of the compound solution is added to disks at concentrations that can vary from 0.001 mg/l to 1142.9 mg/l.

TABLE 10

Antimicrobial activities of Samples 1-4 (repeat test; 50 μl/disk)

| | MIC mg/l | | | | |
|---|---|---|---|---|---|
| ID | Botrytis cinerea | Penicillium expansum | Alternaria altemata | Monilinia fructicola | Glomerella cingulata |
| Sample 1 | 0.6 | 8.9 | >2.2 | 2.2 | — |
| Sample 2 | 2.2 | 8.9 | — | — | — |
| Sample 3 | 1.1 | 8.9 | >2.2 | 1.1 | — |
| Sample 4 | 0.6 | 8.9 | >2.2 | 1.1 | — |

The acetone is permitted to evaporate for 5 minutes. The headspace around the *Botrytis cinerea* inoculum is then sealed inside the well by the film with the adhering disk containing the fungicide. Plates are inverted to prevent any possibility of the chemical from flaking from the disk and falling onto the inoculated agar. After 3 days of incubation at 23° C., cultures are evaluated for percent growth relative to control and determination of MIC. Samples 1-4 show good antimicrobial activity against *Botrytis cinerea* and/or other pathogens in this in vitro analysis. Minimum inhibitory concentrations (MIC) are shown in Tables 9 and 10 for results from two separate tests.

Example 14—Antimicrobial Activity Against Bacteria 12-well (6.5 ml volume per well) microtiter plates are used for the in vitro inhibition assay for volatile antimicrobial compounds. A 3-ml volume of full-strength L$^B$ Agar is added to each well. After cooling, 15 μL of *Escherichia coli*

(ATCC #25922) adjusted to an optical density of 0.02 to 0.035, and further diluted 1/10 is pipetted to the centre of the agar. The plate is tilted to distribute bacteria uniformly. Whatman #1 filter disks (1.5 cm; Cat. No. 1001-0155) are placed on the underside of a polyethylene PCR plate sealing film. For determination of the minimum inhibitory concentration (MIC), test compounds are diluted in acetone, in duplicate, and 50 μl of compound is added to disks at concentrations that can vary from 0.015 to 35.7 mg/l. The acetone is permitted to evaporate for 5 minutes. The headspace around the *Escherichia coli* inoculum is then sealed inside the well by the film with the adhering disk containing the fungicide. Plates are inverted, placed over the treated disks and sealed to prevent any of the chemical from flaking from the disk and falling onto the inoculated agar. After 2 days of incubation at 23° C., cultures were evaluated for colony growth relative to control. Samples 1-4 show good antimicrobial activity against *Escherichia coli* in this in vitro analysis.

Example 15

In order to demonstrate unexpected volatility of compound A (1-hydroxy-5-fluoro-1, 3-dihydro-2, 1-benzoxaborole) and a new method to apply the volatile compound A, another in vivo assay is developed to control *Botrytis cinerea* on strawberry. Eight strawberries (per repetition, in triplicate) are placed in an industry standard 1-lb PET clamshell with the stem-end facing down. A fresh wound on the upwards facing tip of the fruit is then inoculated with 20 μL of $1\times10^5$ spores per mL suspension of *B. cinerea*.

Two identically prepared clamshells per repetition and treatment are then placed at the bottom of a 36-L acrylic desiccator cabinet (Fisher Scientific, No. 08-642-23C), and pre-cooled for 2 hours at 1° C. prior to treatment application. Compound A is then mixed with acetone and 100 μL of the mixture is pipetted into a small glass tube. This tube is then placed inside a pre-heated sublimation device (0.5" OD by 6" long thermostatically heated copper tube mounted to a 0.5 L/min low flow fan) set at 60° C. for 1-minute to allow the acetone to evaporate. Compound A is then introduced into the cabinet containing the clamshell by using the sublimation device set at 180° C. to achieve a final headspace concentration of 0.1 mg/L and equilibrated at 1° C. for 0.5 or 1 hour.

TABLE 11

Valatile application of Compound A to control *B. cinerea* infection

| Clamshell Condition | Treatment Time (hour) | Disease Severity (0 to 4) | | |
|---|---|---|---|---|
| | | Day 1 | Day 3 | Day 5 |
| Untreated | 0 | 1.3 | 3.5 | 4.0 |
| Treated | 0.5 | 0.0 | 0.1 | 2.3 |
| | 1 | 0.0 | 0.0 | 0.4 |
| Untreated (fruit transfer) | 0.5 | 0.0 | 2.7 | 3.4 |
| | 1 | 0.0 | 0.1 | 1.6 |

After incubation, both clamshells are removed from the treatment chamber. One clamshell is undisturbed while the fruit from the second clamshell are immediately transferred into a new untreated clamshell. All clamshells are then held at 1° C. for 5 days and then evaluated during an additional 5 days at 21° C. During the 5 days at 21° C., the fruits are evaluated for gray mold severity (scale 0 to 4, with ≤1 indicating marketable fruit and 4 indicating ≥50% of fruit surface covered by pathogen). The results from Table 11 demonstrate the unexpected volatility of Compound A applied to clamshells and its ability to control *B. cinerea* development on strawberry throughout the 5 days of simulated marketing at 21° C. The treated clamshell produces marketable fruit up to 3 days with 0.5 hour treatment (0.1), whereas fruits in new clamshells are unmarketable (2.7). Similarly, the treated clamshell produces marketable fruit up to 5 days with 1 hour treatment (0.4), whereas fruits in new clamshells are unmarketable (1.6). Thus, treatments where berries remain in the treated clamshells have the best level of control due to the compound further volatilizing over time off of the clamshell surface.

Furthermore, berries that are placed into a new clamshell still benefit from the initial volatile treatment and demonstrated better control of *Botrytis cinerea* than untreated fruit, but the control is less than the treated clamshell since there is no longer any new exposure to the volatile substance off of the treated clamshell surface. Therefore, the results from this study provide evidence that a volatile application of Compound A provides control of fungal pathogen growth (untreated fruit transfer) and that Compound A deposited on clamshell surfaces will subsequently volatilize during 5 days at 21° C., providing additional useful control of *Botrytis cinerea* growth (treated).

Example 16

In order to demonstrate unexpected volatility of Compound A, another in vivo assay is developed to evaluate blue mold (*Penicillium expansum*) control on apple. Two apples are placed in a clamshell, and three fresh wounds are made near the equatorial region of each fruit. Each fruit wound is then inoculated with 20 μL of $1\times10^6$ spores per mL of *Penicillium expansum* suspension. The inoculum is allowed to dry for two hours prior to treatment application as a volatile or contact.

TABLE 12

Comparison of volatile and contact fungicidal activity of Compound A to control *Penicillim expansum* infection

| Assay | Treatment rate (mg/L) | Browning Rot (diameter; mm) | | | |
|---|---|---|---|---|---|
| | | Day 0 | Day 2 | Day 4 | Day 7 |
| Contact | 0 | 0.0 | 6.4 | 15.7 | 29.6 |
| | 2 | 0.0 | 3.7 | 15.5 | 23.3 |
| | 10 | 0.0 | 2.2 | 8.0 | 20.2 |
| | 50 | 0.0 | 0.7 | 5.7 | 15.0 |
| | 250 | 0.0 | 0.0 | 4.3 | 11.8 |
| Volatile | 0 | 0.0 | 6.6 | 16.1 | 30.5 |
| | 0.02 | 0.0 | 0.9 | 2.8 | 6.9 |
| | 0.1 | 0.0 | 0.0 | 0.3 | 2.0 |
| | 0.5 | 0.0 | 0.0 | 0.0 | 0.4 |
| | 2.5 | 0.0 | 0.0 | 0.0 | 0.0 |

Volatile Assay: Clamshells are then placed at the bottom of a 36-L acrylic desiccator cabinet (Fisher Scientific, No. 08-642-23C). Compound A is mixed with acetone and 250 μL of the mixture is pipetted into a small glass tube. This tube is then placed inside a pre-heated sublimation device (0.5" OD by 6" long thermostatically heated copper tube mounted to a 0.5 L/min low flow fan) set at 60° C. for 1 minute to allow the acetone to evaporate. Compound A is then introduced into the cabinets containing the clamshells by using the sublimation device set at 180° C. to achieve a final headspace concentration of 2.5, 0.5, 0.1 or 0.02 mg/L. The chambers are then incubated at 1° C. for 5 days. After incubation, fruits are evaluated by measuring the diameter (mm) of rot development (browning) up to 7 days at 21° C.

Contact Assay: Compound A is dissolved in 85% methanol to achieve a final concentration of 250, 50, 10, or 2 mg/L. A 250 mL solution of each concentration is used to dip two inoculated apples, one minute per apple, performed in triplicate per rate. The dipped fruits are then placed back into the clamshells, which are then placed in a secondary container and incubated at 1° C. for 5 days. After incubation, fruits are evaluated for diameter (mm) of rot development (browning) up to 7 days at 21° C. Table 12 demonstrates the unexpected volatility of Compound A to control *Penicillium expansum* on apples during storage even when applied at 100× lower rate (v/v) than as a contact.

Example 17

In order to demonstrate unexpected volatility of Compound A, another in vivo assay is developed to evaluate gray mold (*Botrytis cinerea*) control on strawberry. Eight strawberries (per repetition, in triplicate) are placed in an industry standard 1-lb PET clamshell with the stem-end facing down. A fresh wound on the upwards facing tip of the fruit is then inoculated with 20 µL of $1 \times 10^5$ spores per mL suspension of *B. cinerea*. The inoculum is allowed to dry for two hours prior to treatment application as a volatile or contact.

TABLE 13

Comparison of volatile and contact fungicidal activity of Compound A to control *Botrytis cinerea* infection

| Assay | Treatment rate (mg/L) | Disease Severity (0 to 4) | | | | |
|---|---|---|---|---|---|---|
| | | Day 0 | Day 1 | Day 2 | Day 3 | Day 4 |
| Contact | 0 | 0.0 | 0.0 | 0.8 | 1.1 | 2.0 |
| | 2 | 0.0 | 0.0 | 0.6 | 1.1 | 1.9 |
| | 10 | 0.0 | 0.0 | 0.0 | 0.3 | 1.0 |
| | 50 | 0.0 | 0.0 | 0.0 | 0.0 | 0.0 |
| | 250 | 0.0 | 0.0 | 0.0 | 0.0 | 0.0 |
| Volatile | 0 | 0.0 | 0.1 | 0.9 | 1.4 | 2.3 |
| | 0.02 | 0.0 | 0.0 | 0.1 | 0.2 | 0.7 |
| | 0.1 | 0.0 | 0.0 | 0.0 | 0.0 | 0.0 |
| | 0.5 | 0.0 | 0.0 | 0.0 | 0.0 | 0.0 |
| | 2.5 | 0.0 | 0.0 | 0.0 | 0.0 | 0.0 |

Volatile Assay: Clamshells are then placed at the bottom of a 36-L acrylic desiccator cabinet (Fisher Scientific, No. 08-642-23C). Compound A is mixed acetone and 250 µL of the mixture is pipetted into a small glass tube. This tube is then placed inside a pre-heated sublimation device (0.5" OD by 6" long thermostatically heated copper tube mounted to a 0.5 L/min low flow fan) set at 60° C. for 1-minute to allow the acetone to evaporate. Compound A is then introduced into the cabinets containing the clamshells by using the sublimation device set at 180° C. to achieve a final headspace concentration of 2.5, 0.5, 0.1 or 0.02 mg/L. The chambers are then incubated at 1° C. for 5 days. After incubation, fruits are evaluated for disease (scale 0 to 4, with ≤1 indicating marketable fruit and 4 indicating ≥50% of fruit surface covered by pathogen) up to 4 days at 21° C.

Contact Assay: Compound A is dissolved in 85% methanol to achieve a final concentration of 250, 50, 10, or 2 mg/L. A 250 mL solution of each concentration is used to dip eight inoculated strawberry fruit for one-minute, performed in triplicate per rate. The dipped fruits are then placed back into the clamshells, which are then placed in a secondary container and incubated at 1° C. for 5 days. After incubation, fruits are evaluated for disease severity (scale 0 to 4, with ≤1 indicating marketable fruit and 4 indicating ≥50% of fruit surface covered by pathogen) up to 4 days at 21° C. Table 13 demonstrates the unexpected volatility of Compound A to control *Botrytis cinerea* on strawberries during storage even when applied at 100× lower rate (v/v) than as a contact.

Example 18

An in vitro assay was performed comparing the volatile and contact activity of various benzoxaborole compounds to demonstrate the activity of compound 10 relative to other similar structures from the chemical class.

Volatile assay: 12-well (6.5 mL volume per well) microtiter plates are used. A 3-mL volume of half strength PDA is added to each well. After cooling, 1 µL of $1 \times 10^5$ spores per mL of *Botrytis cinerea* or *Penicillium expansum* suspension is spotted to the center of the agar. A Whatman #1 filter disk (Cat. No. 1001-0155) is placed, in duplicate, on the underside of a polyethylene PCR plate sealing film. Test compounds are mixed with acetone and the mixtures are added to disks in a dose dependent manner to achieve a final headspace concentration of 35.7 to 0.03 mg/L. The acetone is permitted to evaporate for 5 minutes. The headspace around the inoculum is then sealed inside the well by the film with the adhering disk containing the fungicide. Plates are inverted, placed over the treated disks, and sealed to prevent any of the chemical from flaking from the disk and falling onto the inoculated agar. After 3 days of incubation at 23° C., cultures are evaluated for percent growth relative to the acetone only control.

TABLE 14

Comparison of contact and volatile activity of selected benzoxaborole compounds

| Compound ID | Contact MIC (mg/L) | | Volatile MIC (mg/L) | |
|---|---|---|---|---|
| | B. cinerea | P. expansum | B. cinerea | P. expansum |
| 6 | 2.0 | 2.0 | 4.5 | 17.9 |
| 10* | <0.08 | 0.4 | 0.3 | 2.2 |
| 11* | 10 | 2.0 | 4.5 | 17.9 |
| 31 | 0.4 | 2.0 | 0.6 | 8.9 |
| 33 | 0.4 | 2.0 | 0.6 | 8.9 |
| 34 | 2.0 | 0.4 | 0.6 | 2.2 |
| 121 | 10.0 | 10.0 | 4.5 | 17.9 |
| 124 | 2.0 | 2.0 | 4.5 | 8.9 |
| 130 | 2.0 | 0.4 | 1.1 | 4.5 |
| 132 | 2.0 | 2.0 | 1.1 | 4.5 |
| 135 | 2.0 | 2.0 | 17.9 | >35.7 |

*Compound 10 is identical to Compound A; Compound 11 is identical to Compound B

Contact assay: 6-well (16.5 mL volume per well) microtiter plates are used for an in vitro inhibition assay. Half-strength Potato Dextrose Agar (PDA) is amended with a mixture of one of the test compounds with acetone or methanol to a final concentration of 50 to 0.08 mg/L. A 7.5-mL volume of the amended media is added to each well of the microtiter plate. After drying, 1 µL of $1 \times 10^5$ spores per mL of *B. cinerea* or *P. expansum* suspension is spotted to the center of the agar. The plates are sealed with a clear film and incubated for 3 days at 23° C. After incubation, plates are evaluate for percent growth relative to acetone only control. Results are reported as the minimum inhibitory concentration (MIC) required for 100% control of pathogen growth.

Table 14 shows the MIC results of numerous benzoxaboroles assayed for both contact and volatile activity. Results demonstrate that numerous structures in the benzoxaborole class of compounds have both contact and volatile activity.

TABLE 15

Compounds used in this example

| Compound ID | Benzoxaborole structure |
|---|---|
| 6 | 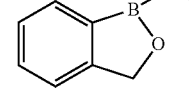 |
| 10* | 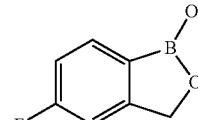 |
| 11* | 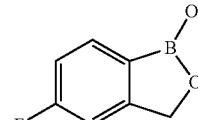 |
| 31 | 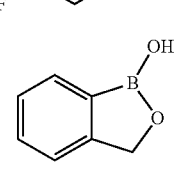 |
| 33 | 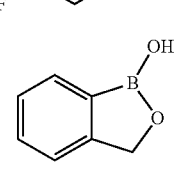 |
| 34 | 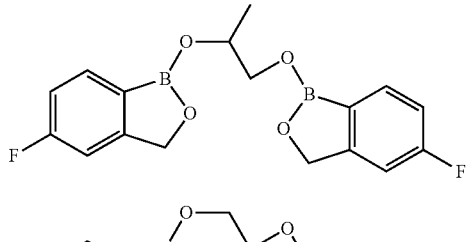 |
| 121 | 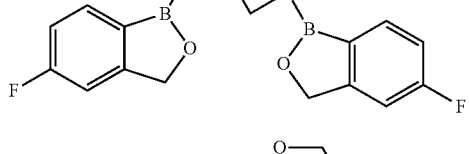 |

TABLE 15-continued

Compounds used in this example

| Compound ID | Benzoxaborole structure |
|---|---|
| 124 | 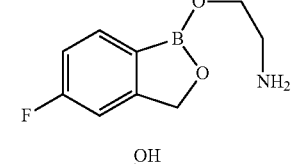 |
| 130 | 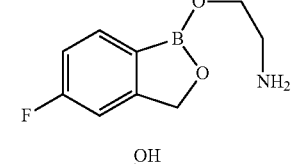 |
| 132 | 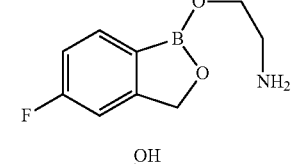 |
| 135 | 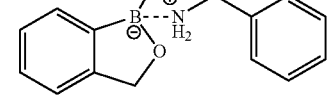 |

*Compound 10 is identical to Compound A;
Compound 11 is identical to Compound B

Example 19

In order to demonstrate unexpected volatility of Compound A, another in vivo assay is developed to evaluate blue mold (*Penicillium expansum*) control on apple and pear, as well as green mold (*Penicillium digitatum*) control on orange. Two apples, pears or oranges are placed in a clamshell, and three fresh wounds are made near the equatorial region of each fruit. Each fruit wound is then inoculated with 20 μL of 1×10$^6$ spores per mL of *Penicillium expansum* or *digitatum* suspension, respectively. The inoculum is allowed to dry for two hours prior to treatment application as a volatile or contact.

TABLE 16

Comparison of Compound A with other fungicides in volatile and contact assays

| | | Apple | | Pear | | Orange |
|---|---|---|---|---|---|---|
| Assay | Test Compound | Browning (mm) | Sporulation (mm) | Browning (mm) | Sporulation (mm) | Sporulation (mm) |
| Volatile | Control (acetone only) | 11.1 | 2.2 | 14.9 | 4.0 | 44.9 |
| | Compound A | 0.4 | 0.0 | 5.7 | 0.0 | 0.0 |
| | Control (ethanol only) | 9.7 | 2.3 | 13.4 | 4.4 | 39.3 |

TABLE 16-continued

Comparison of Compound A with other fungicides in volatile and contact assays

| Assay | Test Compound | Apple | | Pear | | Orange |
| | | Browning (mm) | Sporulation (mm) | Browning (mm) | Sporulation (mm) | Sporulation (mm) |
| --- | --- | --- | --- | --- | --- | --- |
| | Boscalid | 10.3 | 2.4 | 14.3 | 3.6 | 30.3 |
| | Fludioxonil | 11.2 | 3.1 | 12.8 | 2.8 | 40.8 |
| | Imazalil | 11.1 | 3.0 | 14.3 | 3.4 | 41.4 |
| | Pyrimethanil | 11.3 | 2.6 | 14.0 | 6.5 | 22.3 |
| | Thiabendazole | 8.4 | 2.0 | 12.9 | 3.0 | >50 |
| Contact | Control (5% PG only) | 10.3 | 2.6 | 15.1 | 5.4 | >50 |
| | Compound A | 9.9 | 2.3 | 18.9 | 8.4 | >50 |
| | Control (ethanol only) | 9.2 | 5.1 | 8.9 | 1.9 | 9.7 |
| | Boscalid | 7.0 | 0.8 | 8.6 | 2.3 | >50 |
| | Fludioxonil | 2.9 | 0.0 | 3.3 | 0.0 | 8.3 |
| | Imazalil | 6.9 | 0.9 | 7.9 | 1.0 | 0.0 |
| | Pyrimethanil | 8.1 | 2.4 | 8.9 | 5.2 | 0.0 |
| | Thiabendazole | 8.2 | 1.9 | 9.1 | 5.4 | 0.0 |

Volatile Assay: Clamshells are then placed at the bottom of a 2.55-L SnapWare airtight container (Model #109842). An appropriate amount of Compound A (dissolved in acetone), Boscalid, Fludioxinil, Imazalil, Pyrimethanil or Thiabendazole (methanol) is solubilized to achieve a treatment rate of 50 mg/L. (Compound A is not soluble in methanol at room temperature). The solutions are pipetted into Whatman filter disks mounted to the inside lid of the container. The chambers are then incubated at 1° C. for 5 days, removed to 21° C., and evaluated on day 3 by determining the diameter (mm) of rot development (browning) or sporulation.

Contact Assay: Compound A is dissolved in 5% propylene glycol, whereas all other actives are dissolved in 85% methanol at a rate to achieve a final concentration of 250, 50, 10, or 2 mg/L (Compound A is not soluble in methanol at room temperature). A 250 mL solution of each concentration is used to dip two inoculated fruits, one minute per fruit, performed in triplicate per rate. The dipped fruits are then placed back into the clamshells and then into the SnapWare container and incubated at 1° C. for 5 days. The containers are then incubated at 1° C. for 5 days, removed to 21° C., and evaluated on day 3 by determining the diameter (mm) of rot development (browning) or sporulation. Table 16 demonstrates the unexpected volatility of Compound A to control *Penicillium expansum* on apples and pears, as well as *Penicillium digitatum* on oranges. Volatile application of Compound A results in excellent inhibition of browning and sporulation, whereas all other active ingredients result in no or little inhibition. However, contact application of Compound A does not provide good inhibition of browning and sporulation as compared to other fungicides, demonstrating that the volatile application is important for the fungicidal activity of Compound A.

Example 20

In order to demonstrate the volatile activity of Compound A and Compound 31 relative to commercially registered fungicides, an in vitro assay is performed comparing the volatile and contact activity of the active ingredients.

Contact Assay: 12-well (6.5 mL volume per well) microtiter plates are used for the in vitro inhibition assay for Compounds A and 31, and compared to other registered fungicides (5-fluorocytosine, Amphotericin B, Caspofungin diacetate, Fluconazole and Itraconazole). Half-strength Potato Dextrose Agar (PDA) is amended with a mixture of one of the test compounds in acetone or methanol to a final concentration of 50, 10, 2, 0.4 or 0.08 mg/L. A 3-mL volume of the amended media is added to each well of the microtiter plate. After drying, a mycelial plug (5 mm diameter) is aseptically obtained from actively growing cultures of *Epidermophyton floccus*, *Trichophyton rubrum*, or *Trichophyton mentagrophytes* and placed at the center of the plate with the mycelial side in contact with the agar. The plates are sealed with a clear film and incubated inverted for 5 days at 28° C. After incubation, cultures are evaluated (mm diameter growth) for percent growth relative to control with results expressed as minimum inhibitory concentration (MIC) required to control 100% of pathogen growth.

TABLE 17

Comparison of Compounds A and 31 together with other fungicide to control selected fungal pathogens

| | | MIC (mg/L) | | |
| Assay | Test Compound | Epidermophyton floccus | Trichophyton rubrum | Trichophyton mentagrophytes |
| --- | --- | --- | --- | --- |
| Contact | Compound A | 2.0 | 2.0 | 2.0 |
| | Compound 31 | n.d. | 10.0 | 2.0 |
| | 5-Fluorocytosine | >50 | >50 | >50 |
| | Amphotericin B | 50.0 | >50 | >50 |
| | Caspofungin Diacetate | 2.0 | 10.0 | 50.0 |
| | Fluconazole | 10.0 | 50.0 | >50 |
| | Itraconazole | >50 | >50 | >50 |
| Volatile | Compound A | 2.0 | 2.0 | 2.0 |
| | Compound 31 | n.d. | 2.0 | 2.0 |
| | 5-Fluorocytosine | >50 | >50 | >50 |
| | Amphotericin B | >50 | >50 | >50 |
| | Caspofungin Diacetate | >50 | >50 | >50 |
| | Fluconazole | >50 | >50 | >50 |
| | Itraconazole | >50 | >50 | >50 | n.d. = not determined.

Volatile assay: 6-well (16.5 mL volume per well) microtiter plates are used in an in vitro inhibition assay for Compounds A and 31, and compared to other registered fungicides (5-fluorocytosine, Amphotericin B, aspofungin diacetate, Fluconazole and Itraconazole). A 7.5-mL volume of half strength PDA is added to each well. After drying, a mycelial plug (5 mm diameter) is aseptically obtained from actively growing cultures of *Epidermophyton floccus, Trichophyton rubrum,* or *Trichophyton mentagrophytes* and placed at the center of the plate with the mycelial side in contact with the agar. A Whatman #1 filter disk (Cat. No. 1001-325) is placed, in duplicate, on the underside of a polyethylene PCR plate sealing film. For determination of unexpected volatility, test compounds are mixed with acetone or methanol, and then added to disks in a dose dependent manner to achieve a final headspace concentration of 50, 10, 2, 0.4 or 0.08 mg/L. The acetone/methanol is permitted to evaporate for 5 minutes. The headspace around the inoculum is then sealed inside the well by the film with the adhering disk containing the fungicide and incubated inverted for 5 days at 28° C. After incubation, cultures are evaluated for percent growth relative to control with results expressed as minimum inhibitory concentration (MIC) required to control 100% of pathogen growth.

Volatile application of benzoxaboroles of Compounds A and 31 show significant fungicidal activities. Table 17 demonstrates the unexpected volatile activity of Compounds A and 31 with a minimum inhibitory concentration (MIC) of 2 mg/L for both Compound A and 31. In comparison, none of the commercial fungicide standards demonstrated any significant volatile activity where little or no fungicidal activity after volatile applications.

Example 21

In order to demonstrate the volatile activity of Compound 10 (i.e., Compound A) on fungal pathogen species causing human yeast infection, an in vitro assay to measure the rate of growth inhibition was performed. More specifically, growth inhibition of yeast infection fungal species *C. albicans* and *C. krusei* (or *I. orientalis*) by volatile treatment of Compound 10 was assessed via a volatile assay.

Volatile assay: 6-well (16.5 mL volume per well) microtiter plates are used in an in vitro inhibition assay for Compound 10 (i.e., Compound A). A 7.5-mL volume of half strength PDA is added to each well. After drying, a mycelial plug (5 mm diameter) is aseptically obtained from actively growing cultures of *C. albicans* and *C. krusei* (or *I. orientalis*) and placed at the center of the plate with the mycelial side in contact with the agar. A Whatman #1 filter disk (Cat. No. 1001-325) is placed, in duplicate, on the underside of a polyethylene PCR plate sealing film. For determination of unexpected volatility, test Compound 10 is mixed with acetone or methanol, and then added to disks in a dose dependent manner to achieve a final headspace concentration of 35.7, 17.9, 8.9, 4.5, 2.2, 1.1, 0.6, 0.3, 0.1, 0.07, 0.035, and 0.017 mg/L (see Table 18). The acetone/methanol is permitted to evaporate for 5 minutes. The headspace around the inoculum is then sealed inside the well by the film with the adhering disk containing the fungicide and incubated inverted for 5 days at 28° C. After incubation, cultures are evaluated for percent growth relative to control with results expressed as minimum inhibitory concentration (MIC) required to control 100% of pathogen growth.

TABLE 18

MIC (mg/L) of Compound 10 (i.e., Compound A) applied as a volatile against *Candida albicans* and *Issatchenkia orientalis*

| MIC mg/L | Growth Inhibition (%) | |
|---|---|---|
| | *C. albicans* | *C. krusei/ I. orientalis* |
| 35.7 | 100.0 | 100.0 |
| 17.9 | 100.0 | 30.0 |
| 8.9 | 100.0 | 30.5 |
| 4.5 | 100.0 | 22.0 |
| 2.2 | 100.0 | 18.2 |
| 1.1 | 40.2 | −0.2 |
| 0.6 | 22.2 | −5.2 |
| 0.3 | 18.5 | 1.2 |
| 0.1 | 11.9 | 0.4 |
| 0.07 | 7.9 | 0.5 |
| 0.035 | 1.6 | −1.4 |
| 0.017 | 2.0 | −1.3 |

Volatile application of benzoxaboroles of Compound 10 (i.e., Compound A) shows significant fungicidal activities against yeast infection pathogens, *C. albicans* and *C. krusei*. For example, Table 18 demonstrates the unexpected volatile activity of Compound 10 (i.e. Compound A) with a minimum inhibitory concentration (MIC) of 2.2 mg/L for *C. albicans* and a minimum inhibitory concentration (MIC) of 35.7 mg/L for *C. krusei*.

Example 22

An in vivo assay is used to evaluate the ability of Compound A (1-hydroxy-5-fluoro-1, 3-dihydro-2, 1-benzoxaborole) to control fungal growth of seeds.

TABLE 19

Effect of a 10 mg/L headspace treatment of Compound A in controlling *Aspergillus brasiliensis* growth on grains.

| | Fungal growth on PDA (mm) | | |
|---|---|---|---|
| Grains | Compound A | Control-Acetone | Control-No Acetone |
| Barley | 0 | 12.8 | 21.7 |
| Corn Dry | 0 | 10.1 | 22.8 |
| Millet | 0 | 7.2 | 19.1 |
| Rice | 0 | 7.5 | 21.6 |
| Rye | 0 | 8.4 | 21 |
| Wheat | 0 | 8.1 | 22.4 |

Grains consisting of corn, wheat, rice, rye, millet and barley are surface sterilized with 0.825% NaOCl for 1 minute and rinsed thrice with sterile distilled water. The grains are inoculated by soaking them in a $1 \times 10^6$ spores/mL suspension of *Aspergillus brasiliensis* for 1 minute. The excess inoculum is blotted out with a sterile paper towel before plating five seeds in a Petri plate containing 25 mL of PDA. For determination of efficacy, Compound A is diluted in acetone and added to 42.5 mm Whatman #1 filter disks (Cat. No. 1001-042) attached to the inner side of the lid in a dose dependent manner to achieve a final headspace concentration of 0.4, 2, or 10 mg/L. The acetone is permitted to evaporate for five minutes before closing plate and sealing it with parafilm. The plates are incubated at 23° C. for three days. After storage, the grains are evaluated for mycelial colony diameter (mm), with results summarized in Table 19. Results demonstrate 100% control of *Aspergillus brasiliensis* in this in vivo analysis.

We claim:

1. A method of using a volatile antimicrobial compound against pathogens affecting meats, plants, or plant parts, comprising contacting the meats, plants, or plant parts with an effective amount of the volatile antimicrobial compound having a structure of formula (I) or (II):

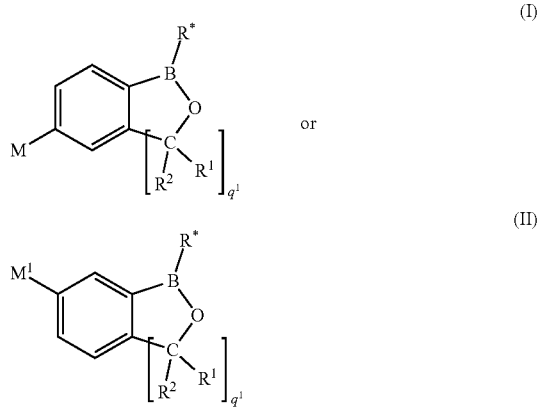

wherein q1 is 1;
M is hydrogen, halogen, —OCH$_3$, or —CH$_2$—O—CH$_2$—O—CH$_3$;
M$^1$ is halogen, —CH$_2$OH, or —OCH$_3$;
R$^1$, and R$^2$ are independently hydrogen, OH, NH$_2$, SH, CN, NO$_2$, SO$_2$, OSO$_2$OH, OSO$_2$NH$_2$, substituted or unsubstituted cycloalkyl, substituted or unsubstituted heterocycloalkyl, substituted or unsubstituted aryl, or substituted or unsubstituted heteroaryl; and
R* is substituted or unsubstituted vinyl;
and agriculturally acceptable salts thereof.

2. The method of claim 1, wherein each of R$^1$ and R$^2$ is H.

3. The method of claim 1, wherein R* is substituted vinyl.

4. The method of claim 3, wherein R* is methyl substituted vinyl.

5. The method of claim 1, wherein R* is unsubstituted vinyl.

6. The method of claim 1, wherein the compound is

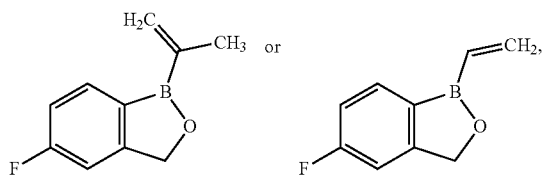

or agriculturally acceptable salts thereof.

7. The method of claim 1, wherein the pathogen is selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp.

8. The method of claim 1, wherein the pathogen is selected from the group consisting of *Erwinia* spp., *Pantoea* spp., *Pectobacterium* spp., *Pseudomonas* spp., *Ralstonia* spp., *Xanthomonas* spp.; *Salmonella* spp., *Escherichia* spp., *Lactobacillus* spp., *Leuconostoc* spp., *Listeria* spp., *Shigella* spp., *Staphylococcus* spp., *Candida* spp., *Debaryomyces* spp., *Bacillus* spp., *Campylobacter* spp., *Clavibacter* spp., *Clostridium* spp., *Cryptosporidium* spp., *Giardia* spp., *Vibrio* spp., *Xanthomonas* spp., and *Yersinia* spp.

9. The method of claim 1, wherein the method comprises a pre-harvest treatment or post-harvest treatment.

10. The method of claim 9, wherein the post-harvest treatment is selected from the group consisting of treatment during field packing, treatment during palletization or after palletization, in open pallets or in wrapped pallets, in tents, in-box treatments with or without liners, in sea container, truck or other container types used during transportation, and treatment during storage (Regular atmosphere or Controlled atmosphere), and/or throughout the distribution network.

11. The method of claim 1, wherein the meats, plants, or plant parts are selected from the group consisting of fruit, vegetables, nursery, turf and ornamental crops.

12. The method of claim 1, wherein the fruit is selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries.

13. The method of claim 1, wherein the contacting comprises applying the volatile antimicrobial compound by ways selected from the group consisting of spray, mist, thermal or non-thermal fogging, drench, gas treatment, and combinations thereof.

14. The method of claim 13, wherein the gas treatment is selected from the group consisting of release from a sachet, release from a synthetic or natural film or fibrous material, release from liner or other packaging materials, release from powder, release from a gas-releasing generator, release using a compressed or non-compressed gas.

15. The method of claim 1, wherein the compound is

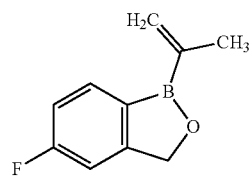

or an agriculturally acceptable salt thereof.

16. The method of claim 1, wherein the compound is
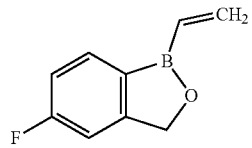
or an agriculturally acceptable salt thereof.
17. The method of claim 1, wherein $M^1$ is halogen.
18. The method of claim 1, wherein M is halogen.
19. The method of claim 3, wherein M is halogen.
20. The method of claim 5, wherein M is halogen.
* * * * *